(12) United States Patent
Yoshida et al.

(10) Patent No.: US 9,987,236 B2
(45) Date of Patent: Jun. 5, 2018

(54) TRANSDERMAL ABSORPTION SHEET, AND MANUFACTURING METHOD FOR THE SAME

(71) Applicant: FUJIFILM Corporation, Tokyo (JP)

(72) Inventors: Junya Yoshida, Ashigarakami-gun (JP); Seiji Kasahara, Ashigarakami-gun (JP); Takayoshi Oyamada, Ashigarakami-gun (JP); Yanlong Che, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/403,588

(22) Filed: Jan. 11, 2017

(65) Prior Publication Data

US 2017/0119691 A1    May 4, 2017

Related U.S. Application Data

(63) Continuation of application No. 14/709,555, filed on May 12, 2015, now Pat. No. 9,649,281, which is a
(Continued)

(30) Foreign Application Priority Data

Nov. 13, 2012    (JP) .................................. 2012-249678

(51) Int. Cl.
*A61K 9/70*    (2006.01)
*A61M 37/00*    (2006.01)
(Continued)

(52) U.S. Cl.
CPC ............ *A61K 9/703* (2013.01); *A61K 8/0204* (2013.01); *A61K 8/732* (2013.01); *A61K 8/735* (2013.01);
(Continued)

(58) Field of Classification Search
None
See application file for complete search history.

(56) References Cited

U.S. PATENT DOCUMENTS

| 2006/0034902 A1 | 2/2006 | Cormier et al. |
| 2008/0269685 A1 | 10/2008 | Singh et al. |

(Continued)

FOREIGN PATENT DOCUMENTS

| CN | 102553064 A | 7/2012 |
| EP | 2283809 A1 | 2/2011 |

(Continued)

OTHER PUBLICATIONS

Kim et al. (Microneedles for drug and vaccine delivery, published online May 1, 2012).*

(Continued)

*Primary Examiner* — Robert A Wax
*Assistant Examiner* — Melissa S Mercier
(74) *Attorney, Agent, or Firm* — Sughrue Mion, PLLC

(57) ABSTRACT

A transdermal absorption sheet and a manufacturing method for the transdermal absorption sheet includes a laminating step of forming a multilayer film with a viscosity difference by forming, on a support, a lower layer containing a first transdermal absorption material and an upper layer containing a drug and a second transdermal absorption material and having a lower viscosity than the lower layer, a filling step of filling needle-like recessed portions corresponding to inverted needle-like protruding portions with a solution of the transdermal absorption material by pressing a mold in which the needle-like recessed portions are arranged in a two-dimensional array, against a surface of the multilayer film supported by the support to allow the multilayer film to flow, a solidifying step of solidifying the multilayer film with the mold pressed against the surface of the multilayer (Continued)

film, and a peeling-off step of peeling the solidified multi-layer film from the mold.

9 Claims, 13 Drawing Sheets

Related U.S. Application Data continuation of application No. PCT/JP2013/080538, filed on Nov. 12, 2013.

(51) Int. Cl.
| | |
|---|---|
| *A61K 8/73* | (2006.01) |
| *A61Q 19/08* | (2006.01) |
| *A61K 8/02* | (2006.01) |
| *A61K 9/00* | (2006.01) |
| *A61K 38/27* | (2006.01) |
| *A61K 38/38* | (2006.01) |
| *B29C 41/22* | (2006.01) |
| *B29C 59/00* | (2006.01) |
| *B29C 59/02* | (2006.01) |
| *B29L 31/00* | (2006.01) |

(52) U.S. Cl.
CPC ............ *A61K 9/0021* (2013.01); *A61K 38/27* (2013.01); *A61K 38/385* (2013.01); *A61M 37/0015* (2013.01); *A61Q 19/08* (2013.01); *B29C 41/22* (2013.01); *B29C 59/005* (2013.01); *B29C 59/022* (2013.01); *A61K 2800/91* (2013.01); *A61M 2037/0023* (2013.01); *A61M 2037/0046* (2013.01); *A61M 2037/0053* (2013.01); *B29C 2059/023* (2013.01); *B29K 2995/0056* (2013.01); *B29K 2995/0065* (2013.01); *B29L 2031/7544* (2013.01)

(56) References Cited

U.S. PATENT DOCUMENTS

| | | | |
|---|---|---|---|
| 2009/0155330 | A1 | 6/2009 | Ghartey-Tagoe et al. |
| 2012/0078189 | A1 | 3/2012 | Ogawa et al. |

FOREIGN PATENT DOCUMENTS

| | | | |
|---|---|---|---|
| JP | 2006-341089 A | | 12/2006 |
| JP | 2008-509747 A | | 4/2008 |
| JP | 2008-194288 A | | 8/2008 |
| JP | 2010-69253 A | | 4/2010 |
| JP | 2010069253 A | * | 4/2010 |
| JP | 2012-196426 A | | 10/2012 |
| JP | 2012-200572 A | | 10/2012 |
| WO | 2009/094394 A1 | | 7/2009 |

OTHER PUBLICATIONS

Chu et al. (Fabrication of Dissolving Polymer Microneedles for Controlled Drug Encapsulation and Delivery: Bubble and Pedestal Microneedle Designs, Journal of Pharmaceutical Sciences, vol. 99, 4228-4238 (2010).*

Kim et al., "Microneedles for drug and vaccine delivery," HHS Public Access, published online May 1, 2012, 55 pages.

Chu et al., "Fabrication of Dissolving Polymer Microneedles for Controlled Drug Encapsulation and Delivery: Bubble and Pedestal Microneedle Designs," Journal of Pharmaceutical Sciences, vol. 99, No. 10, Oct. 2010, pp. 4228-4238.

Communication dated Sep. 1, 2016 from the State Intellectual Property Office of the P.R.C. In counterpart Application No. 201380059212.0.

Communication dated Jan. 19, 2016 from the Japanese Patent Office in counterpart application No. 2014-546987, 6 pages in Japanese and English.

Communication dated Jun. 9, 2016 from the European Patent Office issued in corresponding Application No. 13855673.3.

International Preliminary Report on Patentability and Written Opinion, dated May 28, 2015, issed in corresponding International Application No. PCT/JP2013/080538, 14 pages in English and Japanese.

International Search Report for PCT/JP2013/080538 dated Feb. 25, 2014, 3 pages in English.

Written Opinion for PCT/JP2013/080538 dated Feb. 25, 2014, 5 pages.

* cited by examiner (A)

| | VISCOSITY OF UPPER LAYER (a) | VISCOSITY OF LOWER LAYER (b) | b/a | FILLING RATE | RANK |
|---|---|---|---|---|---|
| EXAMPLE 1 | 2Pa·s | 1000Pa·s | 500 | 81% | A |
| EXAMPLE 2 | 2Pa·s | 200Pa·s | 100 | 80% | A |
| EXAMPLE 3 | 2Pa·s | 10Pa·s | 5 | 62% | B |
| EXAMPLE 4 | 30Pa·s | 1000Pa·s | 33 | 75% | B |
| EXAMPLE 5 | 10Pa·s | 200Pa·s | 20 | 82% | A |
| EXAMPLE 6 | 2Pa·s | 1000Pa·s | 500 | 82% | A |
| EXAMPLE 7 | 2Pa·s | 1000Pa·s | 500 | 81% | A |
| EXAMPLE 8 | 2Pa·s | 1000Pa·s | 500 | 80% | A |
| EXAMPLE 9 | 2Pa·s | 1000Pa·s | 500 | 85% | A |
| COMPARATIVE EXAMPLE 1 | 2Pa·s | 2Pa·s | 1 | 51% | C |
| COMPARATIVE EXAMPLE 2 | 200Pa·s | 10Pa·s | 0.05 | 20% | D |

TRANSDERMAL ABSORPTION SHEET, AND MANUFACTURING METHOD FOR THE SAME

CROSS-REFERENCE TO RELATED APPLICATIONS

This application is a Continuation of U.S. patent application Ser. No. 14/709,555, filed May 12, 2015, which is a Continuation of PCT International Application No. PCT/JP2013/080538 filed on Nov. 12, 2013, which claims priority under 35 U.S.C §119(a) to Japanese Patent Application No. 2012-249678 filed on Nov. 13, 2012. Each of the above application(s) is hereby expressly incorporated by reference, in its entirety, into the present application.

BACKGROUND OF THE INVENTION

Field of the Invention

The present invention relates to a transdermal absorption sheet and a method for manufacturing the transdermal absorption sheet and in particular, to a technique for concentrating a drug at microneedles.

Description of the Related Art

Conventionally, methods for administering a medicine (drug) or the like through a biological surface, that is, the skin or mucosa mostly involve attaching mainly an aqueous material or a powdery material. However, since an attachment area for these materials is limited to the surface of the skin, perspiration, contact with foreign matter, or the like may cause the attached medicine or the like to be removed, and administering an appropriate amount of medicine is difficult. Furthermore, in allowing the medicine to permeate deep through the skin, it is difficult to reliably control a depth of penetration using a method that utilizes permeation by diffusion of a medicine as described above. Thus, obtaining sufficient drug efficacy has been difficult.

Because of such a situation, a method has been carried out in which a transdermal absorption sheet provided with microneedles (needle-like protruding portions) having a high aspect ratio and containing a drug is used to inject a medicine through the microneedles inserted into the skin. In order to make the transdermal absorption sheet available, the drug needs to be mixed into the transdermal absorption sheet. However, drugs are expensive in many cases, and thus, the drug needs to be contained in the transdermal absorption sheet so as to concentrate at the microneedles.

A method for manufacturing a transdermal absorption sheet is described in, for example, Japanese Patent Laid-Open No. 2010-69253 (Patent Literature 1) and Japanese Patent Laid-Open No. 2008-194288 (Patent Literature 2).

Patent Literature 1 discloses a manufacturing method for a transdermal absorption sheet which involves feeding and solidifying a material solution containing a drug in a mold in which inverted shapes of microneedles are formed and then feeding and solidifying a material solution containing no drug in the mold. According to Patent Literature 1, this allows the drug to efficiently concentrate at the microneedle.

Patent Literature 2 is not a technique for efficiently concentrating the drug at the microneedles but is a technique for improving sustained release of the drug. According to Patent Literature 2, needle-like components are manufactured as follows. That is, Patent Literature 2 discloses a method for manufacturing needle-like components by applying an easily decomposable material to a substrate, then selectively applying a projecting portion material only to a portion corresponding to needle-like recessed portions of the mold or applying the projecting portion material all over the mold to obtain a coating layer, then pressing a recessed plate provided with inverted shapes of needle-like protruding portions against the coating layer, and thereafter peeling the recessed plate off from the substrate. According to Patent Literature 2, this enables transdermal administration with sustained release and needle-like components with a sufficient mechanical strength can be manufactured.

SUMMARY OF THE INVENTION

However, in the manufacturing method in Patent Literature 1, in the filling s of filling the mold with the material solution, the filling is performed in two steps of: filling the mold with the material solution containing the drug; and filling the mold with the material solution containing no drug. Thus, the method may include an increased number of manufacturing steps and have degraded production efficiency.

On the other hand, the manufacturing method in Patent Literature 2 needs a single filling step and has improved production efficiency compared to the manufacturing method in Patent Literature 1. However, the manufacturing method in Patent Literature 2 is disadvantageous in that, since the projecting portion material is selectively applied to micro areas each having a size of approximately 300 μm (a general value for the inlet diameter of a needle-like recessed portion) corresponding to needle-like recessed portions two-dimensionally arranged in the mold, the application is a complicated and time-consuming step. Furthermore, when the projecting portion material is applied all over the mold, the complicatedness of the application can be avoided, but the needle-like recessed portions cannot be tilled with the projecting portion material in a concentrated manner. That is, it is difficult to achieve concentration of the drug at the microneedles, which is a problem to be solved by the present invention, simply by applying the technique in Patent Literature 2.

The present invention has been developed in view of these circumstances. The present invention aims to provide a transdermal absorption sheet and a manufacturing method for the transdermal absorption sheet that allow the drug to concentrate at the microneedles, while serving to improve production efficiency.

In order to accomplish the object, an aspect of the present invention provides a manufacturing method for a transdermal absorption sheet in which a plurality of fine needle-like protruding portions are arranged in a two-dimensional array on a surface of a sheet portion supported by a support, the method comprising: a laminating step of forming, on the support, a multilayer film which comprises a plurality of layers containing a transdermal absorption material, wherein the plurality of layers satisfy $V_1 > V_2 \geq \ldots \geq V_n \geq \ldots \geq V_t$ when a lowermost layer is represented as a first layer, an uppermost layer is represented as a t-th layer ($t > 2$) and a viscosity of an n-th layer is represented as $V_n$, wherein at least one layer other than the lowermost layer contains a drug; a filling step of pressing a mold in which needle-like recessed portions corresponding to inverted needle-like protruding portions are arranged in a two-dimensional array, against a surface of the multilayer film supported by the support to allow the multilayer film to flow and filling the needle-like recessed portions with a solution of the transdermal absorption material; a solidifying step of solidifying the multilayer film in a state where the mold is pressed against the surface of the multilayer film; and a peeling-off step of peeling the solidified multilayer film from the mold.

According to an aspect of the present invention, in the laminating step, on the support, the multilayer film is formed which has the plurality of layers containing the transdermal absorption material. In the multilayer film, when the lowermost layer is represented as the first layer, the uppermost layer is represented as the t-th layer (t≥2), and the viscosity of the n-th layer is represented as Vn, V1>V2≥ . . . ≥Vn≥ . . . ≥Vt is satisfied, and at least one layer other than the lowermost layer contains the drug.

In view of production efficiency, preferably t=2 or 3, and more preferably t=2.

Moreover, in the filling step, a mold in which needle-like recessed portions corresponding to inverted needle-like protruding portions are arranged in a two-dimensional array, is pressed against a surface of the multilayer film supported by the support to allow the multilayer film to flow, thereby filling the needle-like recessed portions with a solution of the transdermal absorption material.

In this filling step, since the viscosity of layers in the laminated multilayer film becomes lower in higher layers, when the mold is pressed against the surface of the multilayer film, firstly, the transdermal absorption material solution in the t-th layer with the lowest viscosity flows into the needle-like recessed portions. Thus, only the transdermal absorption material solution in the t-th layer with the lowest viscosity is filled into the needle-like recessed portions of the mold.

When the mold is further pressed against the surface of the multilayer film, the transdermal absorption material solution in the (t-1)-th layer with a next higher viscosity than the t-th layer acts to flow into the needle-like recessed portions. Thus, the transdermal absorption material solution in the t-th layer having already reached the middle of each of the needle-like recessed portions is pushed toward a tip side of the needle-like recessed portion. By repeating this process, finally, the transdermal absorption material solution in the first layer with the highest viscosity is filled into the needle-like recessed portions. Consequently, the drug can be concentrated at the needle-like protruding portions in the molded transdermal absorption sheet.

Moreover, in the solidifying step, the multilayer film is solidified in a state where the mold is pressed against the surface of the multilayer film. Consequently, even when the filled transdermal absorption material solution is solidified and contracted in the needle-like recessed portions, the transdermal absorption material solution is pressed toward the tip side of each needle-like recessed portion by a pressing force. Thus, the shape of the needle-like recessed portion can be accurately transferred. Moreover, in the present invention, the filling is completed in one single filling step, leading to improved production efficiency.

In many cases, a drug to be used has the risk of being thermally decomposed, and thus, the laminating step, the filling step, and the peeling-off step of the present invention are preferably executed at normal temperature. Furthermore, also when the solidifying step is executed by means of drying, drying temperature is preferably low enough to prevent the drug from being decomposed.

In an aspect of the present invention, a viscosity of the lowermost layer is preferably at least twice as high as a viscosity of the uppermost layer, more preferably at least five times as high as the viscosity of the uppermost layer, particularly preferably at least 10 times as high as the viscosity of the uppermost layer, and most preferably at least 20 times as high as the viscosity of the uppermost layer. In order to achieve both the coatability (coating property) and flowability of the uppermost layer and the lowermost layer, the viscosity of the lowermost layer is preferably at most 1,000 times as high as the viscosity of the uppermost layer.

When the viscosity of the lowermost layer is at least twice as high as the viscosity of the uppermost layer, it is possible to increase a time difference between the start of flow of the transdermal absorption material solution in the uppermost layer and the start of flow of the transdermal absorption material solution in the lowermost layer. This allows the needle-like recessed portions to be filled with the transdermal absorption material solution in the uppermost layer in a concentrated manner. In this case, the viscosity of the uppermost layer is preferably 2 to 30 Pa·s.

Thus, the drug can further be concentrated at the microneedles.

In the present invention, an inlet portion of each needle-like recessed portion in the mold preferably has a tapered portion with a tapered shape.

Thus, when the mold is pressed against the surface of the multilayer film to allow the transdermal absorption material solution in the uppermost layer to flow, the transdermal absorption material solution in the uppermost layer collects in the tapered portion. Consequently, the transdermal absorption material solution in the uppermost layer can be easily filled into the needle-like recessed portion. This also applies to other transdermal absorption material solutions.

In an aspect of the present invention, preferably, a bottom surface of each tapered portion is formed into a hexagon, and the needle-like recessed portions with the tapered portions are arranged so as to form a honeycomb structure.

Thus, the adjacent needle-like recessed portions are easily evenly filled with the transdermal absorption material by a pressure that presses the mold against the surface of the multilayer film.

In an aspect of the present invention, preferably, the pressing surface of the mold is provided with enclosing members that evenly partition the area of the multilayer film to be fed into the adjacent needle-like recessed portions into areas so that the enclosing members protrude from the pressing surface.

Thus, when the mold is pressed against the surface of the multilayer film, a filling amount of transdermal absorption material solution is accurately evenly distributed to the individual needle-like recessed portions. Consequently, a possible variation among the plurality of molded needle-like recessed portions can be prevented.

Furthermore, particularly preferably, the enclosing members and the tapered portions arranged in a honeycomb shape are combined together.

In an aspect of the present invention, preferably, an air vent hole is formed at a tip of the needle-like recessed portion. This allows each of the needle-like recessed portions to be easily filled with the transdermal absorption material solution up to the tip. in this case, the diameter of the air vent hole is preferably 1 to 50 μm. When the diameter is less than 1 μm, the air vent hole fails to sufficiently fulfill the functions as an air vent. When the diameter exceeds 50 μm, the sharpness of the molded needle-like protruding portions is degraded.

Thus, in an aspect of the present invention, preferably, the transdermal absorption material is a water-soluble polymer substance.

Preferably, the water-soluble polymer substance is any one of hydroxyethyl starch, dextran, chondroitin sulfate, hyaluronic acid, and carboxymethyl cellulose.

Furthermore, preferably, the drug is peptide, protein, nucleic acid, polysaccharide, a vaccine, a medical compound belonging to a water-soluble low-molecular-weight compound, or a cosmetic component.

As the water-soluble polymer substance used for the layer containing the drug, one that does not interact with the contained drug is preferably used. For example, if protein is used as the drug, when a chargeable polymer substance is mixed with the protein, the protein and the polymer substance electrostatically interact with each other to form an aggregate, which is cohered and precipitated. Therefore, when a chargeable substance is used as the drug, a water-soluble polymer substance with no charge such as hydroxyethyl starch or dextran is preferably used.

To accomplish the object, another aspect of the present invention provides a transdermal absorption sheet in which a plurality of fine needle-like protruding portions are arranged in a two-dimensional array on a surface of a sheet portion supported by a support, wherein a tip of each of the needle-like protruding portions contains a drug and hydroxyethyl starch, and a base of each of the needle-like protruding portions contains hydroxyethyl starch and hyaluronic acid.

To accomplish the object, yet another aspect of the present invention provides a transdermal absorption sheet in which a plurality of fine needle-like protruding portions are arranged in a two-dimensional array on a surface of a sheet portion supported by a support, in which a tip of each of the needle-like protruding portions contains a drug and chondroitin sulfate, and a base of each of the needle-like protruding portions contains hydroxyethyl starch.

The transdermal absorption sheet according to the yet another aspect of the present invention allows construction of a transdermal absorption sheet with microneedles which can be easily stuck into the skin and which are hard to break.

The transdermal absorption sheet and the manufacturing method therefor according to the present invention can provide a manufacturing method for a transdermal absorption sheet which enables the drug to concentrate at the needle-like protruding portions, while improving production efficiency.

BRIEF DESCRIPTION OF THE DRAWINGS

FIG. 13 is a diagram showing a filling rate in examples and comparative examples.

DETAILED DESCRIPTION OF THE EMBODIMENTS

Preferred embodiments of a transdermal absorption sheet and a manufacturing method for the transdermal absorption sheet according to the present invention is described below in detail using the drawings.

[Needle-like Protruding Portions on the Transdermal Absorption Sheet]

Figure 1:
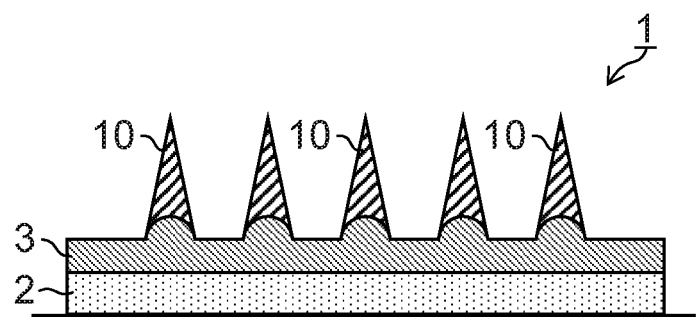
FIG. 1 is a diagram illustrating a structure of a transdermal absorption sheet according to an embodiment of the present invention.

FIG. 1 is a structure diagram of a transdermal absorption sheet 1 of an embodiment of the present invention.

The transdermal absorption sheet 1 of the embodiment of the present invention includes a support 2, a sheet portion 3, and a plurality of microneedles 10 (needle-like protruding portions) arranged in a two-dimensional array on a surface of the sheet portion 3.

The transdermal absorption sheet 1 is configured such that: a tip of the microneedle 10 contains a drug and a transdermal absorption material forming the microneedle and a base of the microneedle 10 contains a transdermal absorption material forming the sheet portion 3.

That is, the transdermal absorption sheet preferably has a structure in which the transdermal absorption material forming the sheet portion 3 enters into the base of the microneedle 10, instead of a structure in which the transdermal absorption material forming the microneedle 10 and the transdermal absorption material forming the sheet portion 3 are definitely separated from each other as the portion of the microneedle 10 and the portion of the sheet portion 3, respectively. This allows formation of the transdermal absorption sheet 1 with the microneedles 10 which can be easily stuck into the skin and which are hard to break.

Figure 2A:
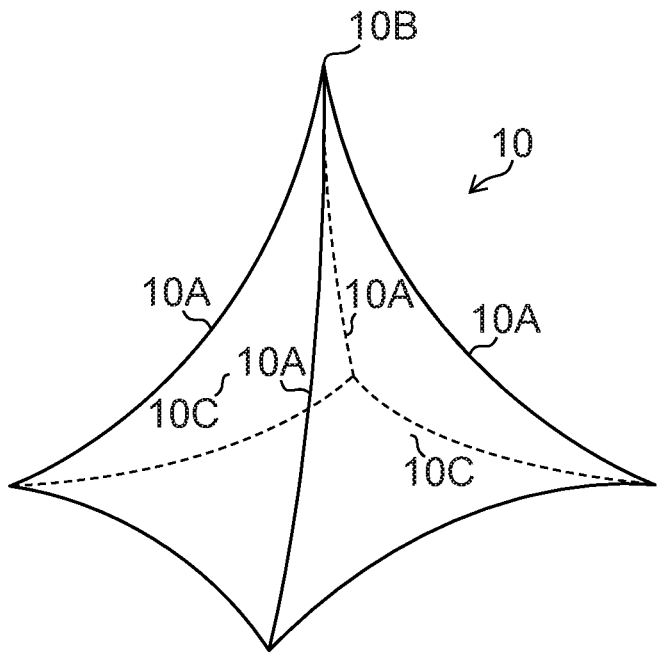
FIG. 2A is a perspective view of a quadrangular pyramidal microneedle structure in the transdermal absorption sheet.
Figure 2B:
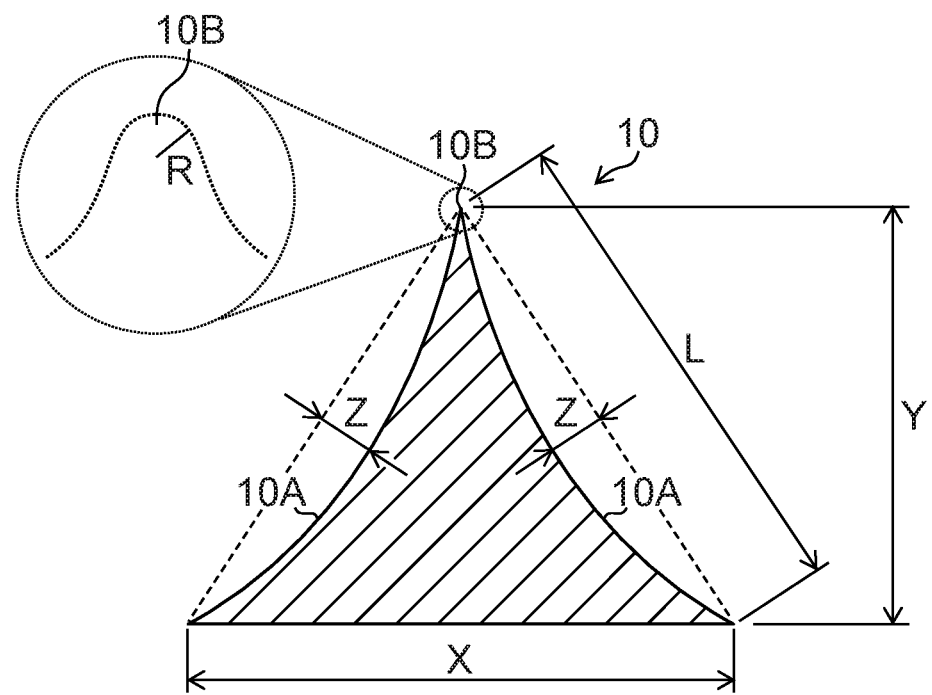
FIG. 2B is a cross-sectional view of the quadrangular pyramidal microneedle structure in the transdermal absorption sheet.

FIG. 2A and FIG. 2B depict a preferred structure of the microneedle 10.

As depicted in a perspective view in FIG. 2A and a cross-sectional view in FIG. 1B, the microneedle 10 formed on the transdermal absorption sheet 1 needs to be shaped as follows so as to be stuck several hundred μm deep into the surface of the skin: (1) The tip is sufficiently pointed, and the diameter of the needle penetrating the skin is sufficiently small (the aspect ratio of length/diameter is high), and (2) the microneedle has a sufficient strength (the microneedle does not bend).

Thus, to meet the requirement in (1), a thin and pointed shape is needed. However, this is opposed to (2), and an excessively thin needle is bent at the tip or root thereof, whereas an excessively thick needle fails to be stuck into the skin. Thus, as depicted in FIG. 2A, a ridge line 10A of the microneedle 10 is preferably shaped to be curved toward the inside of the microneedle. The microneedle with such a shape can be made difficult to bend by sufficiently sharpening the tip, while widening the root. Furthermore, the ridge lines 10A, 10A of a quadrangular pyramidal microneedle preferably extend from a quadrangular pyramidal surface 10C between the ridge lines 10A, 10A.

As for the shape of the microneedle 10, it is preferable that one side X of a bottom surface is in a range of 0.1 μm or more and 1,000 μm or less on, and a height Y is in a range of 0.3 μm or more and 3,000 μm or less. More preferably, one side X of the bottom surface is in a range of 10 μm or more and 400 μm or less, and the height is in a range of 30 μm or more and 1,200 μm or less.

When the length of a segment connecting a start point and an end point of the ridge line is represented as L, the maximum depth Z of curve of the ridge line 10A is preferably 0.04×L or more and 0.2×L or less. Furthermore, the radius of curvature R of a microneedle tip 10B, which indicates sharpness of the microneedle 10, is preferably 20 μm or less, and more preferably 10 μm or less.

Figure 3A:
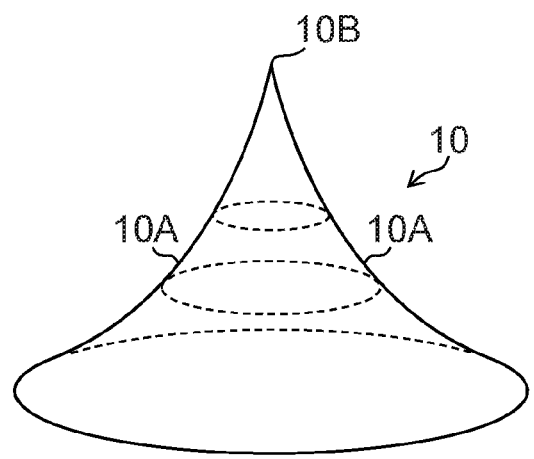
FIG. 3A is a cross-sectional view of a conical microneedle structure in the transdermal absorption sheet.
Figure 3B:
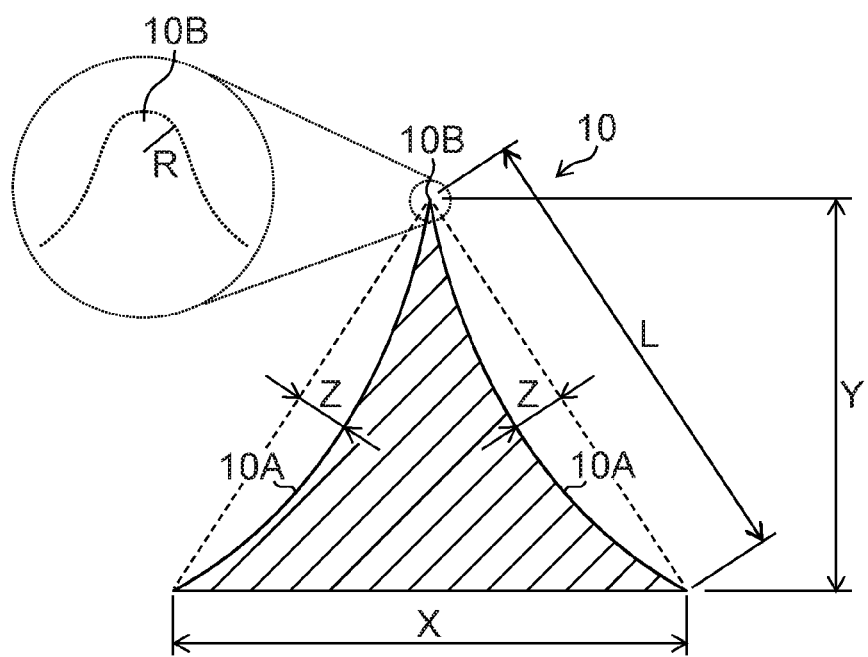
FIG. 3B is a cross-sectional view of the conical microneedle structure in the transdermal absorption sheet.

FIG. 2A and FIG. 2B depict the quadrangular pyramidal microneedle 10, but a microneedle shaped like a cone depicted in FIG. 3A and FIG. 3B and microneedles shaped like other pyramids such as a triangular pyramid preferably have similar sizes. When the microneedle has a conical shape, the diameter X of the bottom surface is preferably within a range of 0.1 μm or more and 1,000 μm or less, and more preferably 50 μm or more and 500 μm or less. Furthermore, when the length of a segment connecting a start point and an end point of generatrix of the cone is represented as L, the maximum depth Z of curve of the cone is preferably 0.04×L or more and 0.2×L or less.

As described above, the transdermal absorption sheet 1 is a protruding portion array in which the microneedles 10 are arranged in a two-dimensional array. To allow the microneedle 10 to be easily stuck into the surface of the skin, it is important to sufficiently sharpen the microneedle tip 10B. The radius of curvature R of the microneedle tip 10B is preferably 10 μm or less. In order to form a microneedle 10 having a tip with a radius of curvature R of 10 μm or less, an important point is whether a solution of a transdermal absorption material can be injected down to the tip (bottom) of needle-like recessed portions corresponding to an inverted shape of the protrusion array formed in the mold so as to allow accurate transfer.

Furthermore, the transdermal absorption sheet needs to contain a drug, but the drug is expensive in many cases. Thus, it is economically important to contain the drug in the transdermal absorption sheet so that the drug concentrates at the portion of each microneedle.

[Manufacturing Method for the Transdermal Absorption Sheet]

A manufacturing method for the transdermal absorption sheet 1 according to the embodiment of the present invention is described.

<Production of the Mold>

Figure 4A:
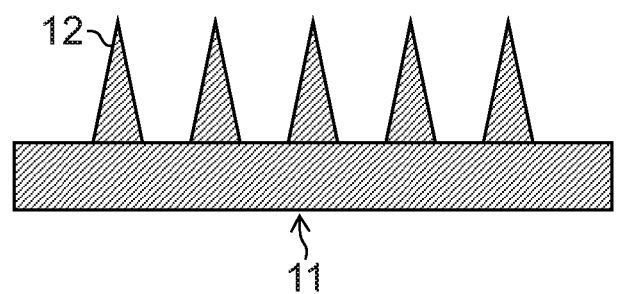
FIG. 4A is a diagram illustrating a production method for a mold.
Figure 4B:
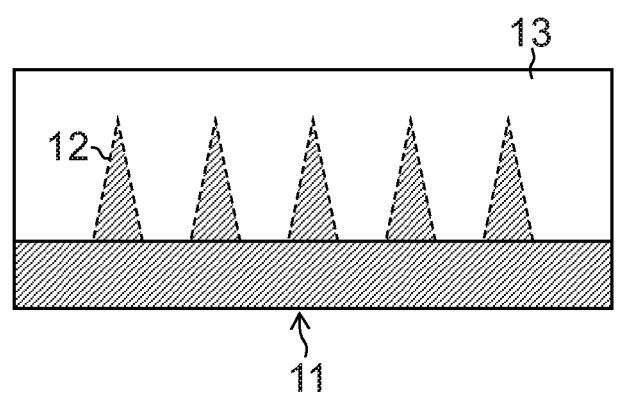
FIG. 4B is a diagram illustrating the production method for the mold.
Figure 4C:
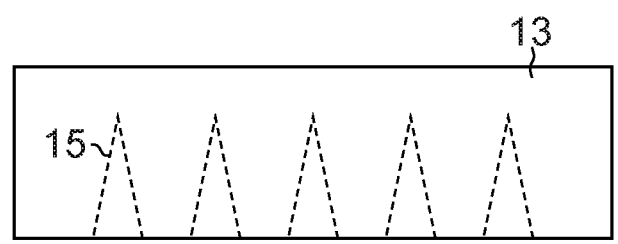
FIG. 4C is a diagram illustrating the production method for the mold.

FIGS. 4A to 4C are process diagrams illustrating production of a mold.

As depicted in FIG. 4A, an original plate 11 is first produced which is used to produce a mold 13 that allows the transdermal absorption sheet 1 to be manufactured.

Two types of methods for producing the original plate 11 are available. A first method is to apply photo resist onto a Si substrate and then to expose and develop the photo resist. Then, etching such as RIE (Reactive Ion Etching) is performed on the photo resist to form an array of conical shape portions 12 (corresponding to the microneedles 10) on a surface of the original plate 11. When etching such as RIE is performed so as to form the conical shape portions 12 on the surface of the original plate 11, the conical shape portions 12 can be formed by carrying out the etching in an oblique direction while the Si substrate is being rotated.

A second method is a method of machining a metal substrate such as Ni using a cutting tool such as a diamond byte to form an array of the shape portions 12 (corresponding to the microneedles 10) shaped like quadrangular pyramids or the like on the surface of the original plate 11.

Then, the mold 13 is produced. Specifically, as depicted in FIG. 4B, the mold 13 is produced from the original plate 11. A method based on Ni electrocasting is used for normal production of the mold 13. Since the original plate 11 has the shape portions of cones or pyramids (quadrangular pyramids, for example) with pointed tips, four methods are possible which allow the original plate 11 to be peeled off from the mold 13 after shape of the original plate 11 is precisely transferred to the mold 13 and which enable the mold 13 to be inexpensively manufactured.

A first method is a method of pouring, into the original plate 11, a silicone resin containing PDMS (polydimethylsiloxane, for example, Sylgard (trademark) 184 manufactured by Dow Corning Toray Co., Ltd.) with a curing agent added thereto, heating and curing the silicone resin at 100° C., and then peeling the silicon resin off from the original plate 11. A second method is a method of pouring, into the original plate 11, a UV curing resin that is cured when irradiated with ultraviolet light in a nitrogen environment, and then peeling the UV curing resin off from the original plate 11. A third method is a method of pouring a solution of a plastic resin such as polystyrene and PMMA (polymethylmethactylate) dissolved into an organic solvent, into the original plate 11 coated with a release agent, volatilizing the organic solvent by means of drying to cure the plastic resin, and then peeling the plastic resin off from the original plate 11. A fourth method is a method of producing an inverted article by means of Ni electrocasting.

Thus, the mold 13 is produced in which needle-like recessed portions 15 that are inverted shapes of cones or pyramids on the original plate 11 are arranged in a two-dimensional array. The mold 13 produced as described above is depicted in FIG. 4C. The mold 13 can be easily produced any number of times using any one of the above-described four methods.

Figure 5:
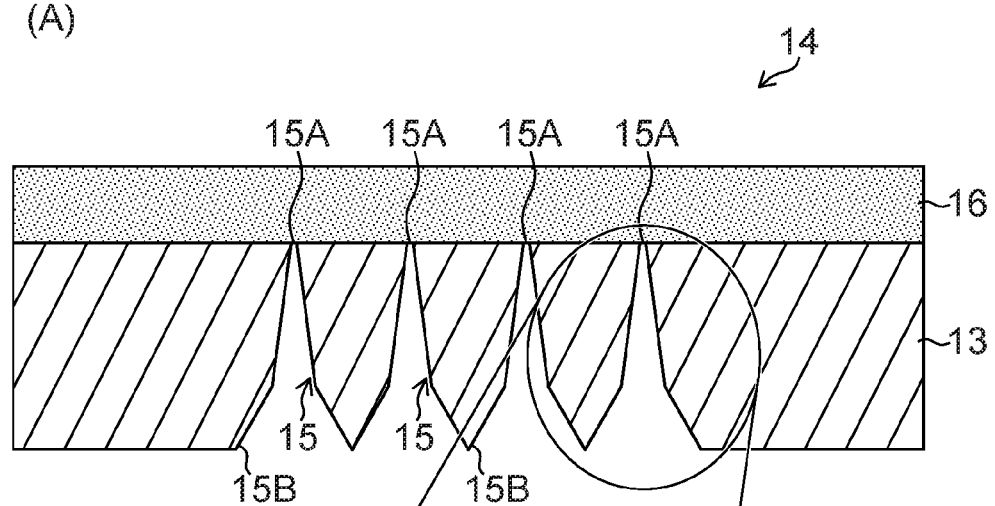
FIG. 5 is a diagram illustrating a mold complex.
Figure 5:
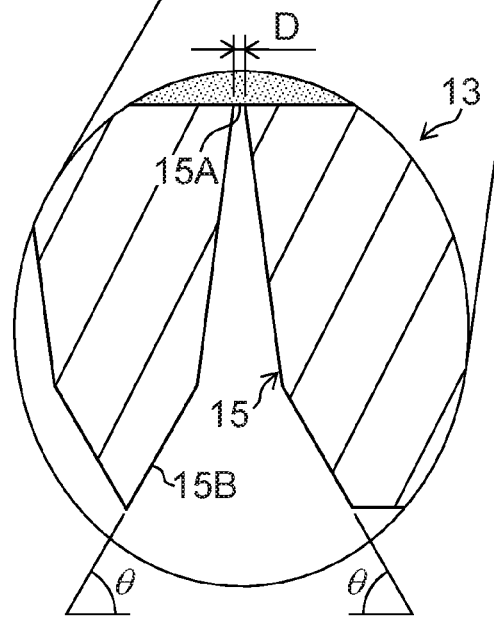

FIG. 5 depicts an aspect of a mold complex 14 that is more preferable in executing the manufacturing method for the transdermal absorption sheet 1 in the embodiment of the present invention, Portion (A) of FIG. 5 depicts a cross-sectional view of the mold complex 14, portion (B) of FIG. 5 depicts an enlarged view of the portion surrounded by the circle in portion (A). As shown in FIG. 5, the mold complex 14 includes the mold 13 in which an air vent hole 15A is formed at the tip (bottom) of each needle-like recessed portion 15 and a gas permeable sheet 16 laminated to a back surface of the mold 13 and formed of a material that allows gas to pass though, while preventing liquid from passing through. The air vent hole 15A is formed as a through-hole that penetrates the back surface of the mold 13. In this regard, the back surface of the mold 13 refers to a surface on the side of the tip of the needle-like recessed portion 15. Thus, the tip of the needle-like recessed portion 15 communicates with the atmosphere via the air vent hole 15A and the gas permeable sheet 16.

The use of the mold complex 14 as described above allows only the air present in the needle-like recessed portions 15 to he removed from the needle-like recessed portions 15 while preventing permeation of the transdermal absorption material solution contained in the needle-like recessed portions 15. Thus, each needle-like recessed portion 15 can be filled with the solution of the transdermal absorption material down to the tip (bottom) of the recessed portion. Consequently, the shape of the needle-like recessed portion 15 can be precisely transferred to the transdermal absorption material, allowing sharper microneedles 10 (needle-like protruding portions) to be formed.

The diameter D of the air vent hole 15A is preferably within a range of 1 to 50 μm. When the diameter D is less than 1 μm, the air vent holes 15A cannot sufficiently accomplish the functions thereof. When the diameter D is more than 50 μm, it is likely that the sharpness of the tip of the molded microneedle 10 is degraded.

A gas permeable sheet 16 formed of a material that allows gas to permeate while preventing liquid from permeating, for example, latex (Asahi Kasei Chemicals Corporation) may be suitably used.

Furthermore, the needle-like recessed portion 15 preferably has a tapered portion 15B with a tapered shape at an inlet portion of the needle-like recessed portion 15, The angle θ of the tapered portion 15B is preferably within a range of 10° to 20°. This taper angle range allows a pressing force to be exerted when the mold 13 is pressed against a surface of a two-layer film during a filling step described below, and also allows the transdermal absorption material solution to be well guided so as to collect in the needle-like recessed portions 15.

Figure 6:
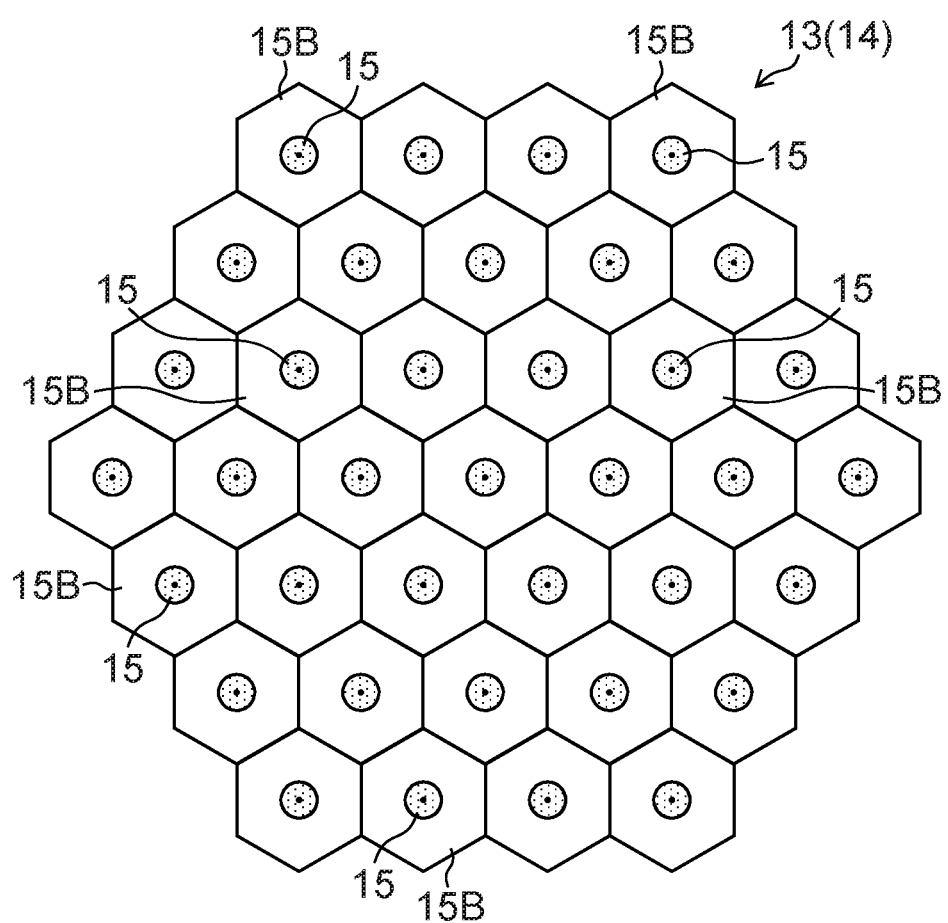
FIG. 6 is a diagram illustrating a mold in which microneedle structures with tapered portions shaped like regular hexagons are arranged in a honeycomb manner.

In this case, preferably, the bottom surface shape of the tapered portion 15B is formed like a hexagon, and the needle-like recessed portions 15 with the tapered portions 15B are arranged so as to form a honeycomb structure, as depicted in FIG. 6. Thus, a pressing force is exerted when the mold 13 or the mold complex 14 is pressed against a surface of a two-layer film 20, facilitating even (uniform) filling of the adjacent needle-like recessed portions 15 with the transdermal absorption material.

Figure 7:
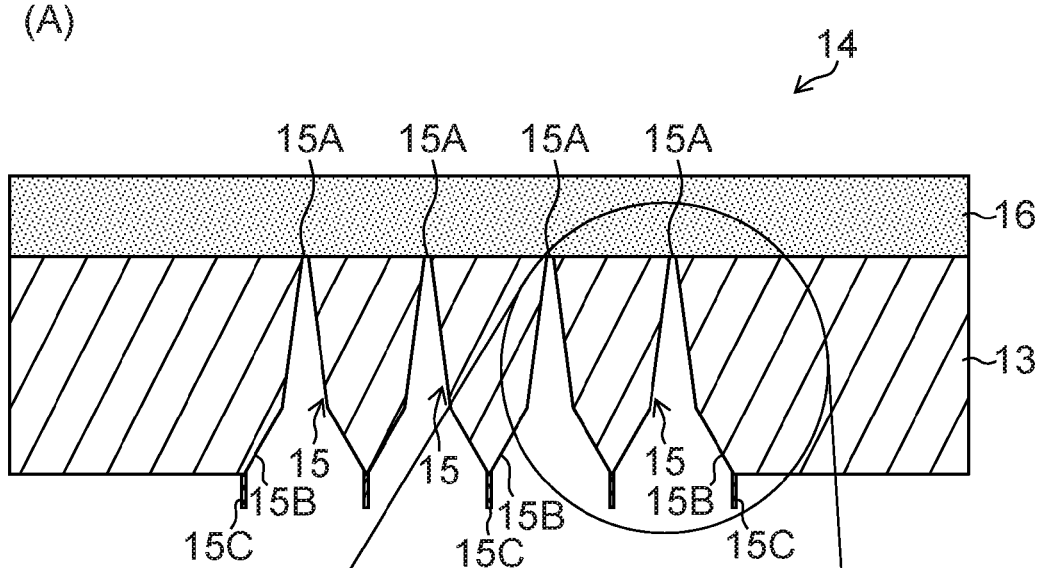
FIG. 7 is a diagram illustrating that enclosing members are formed on the microneedle structures.
Figure 7:
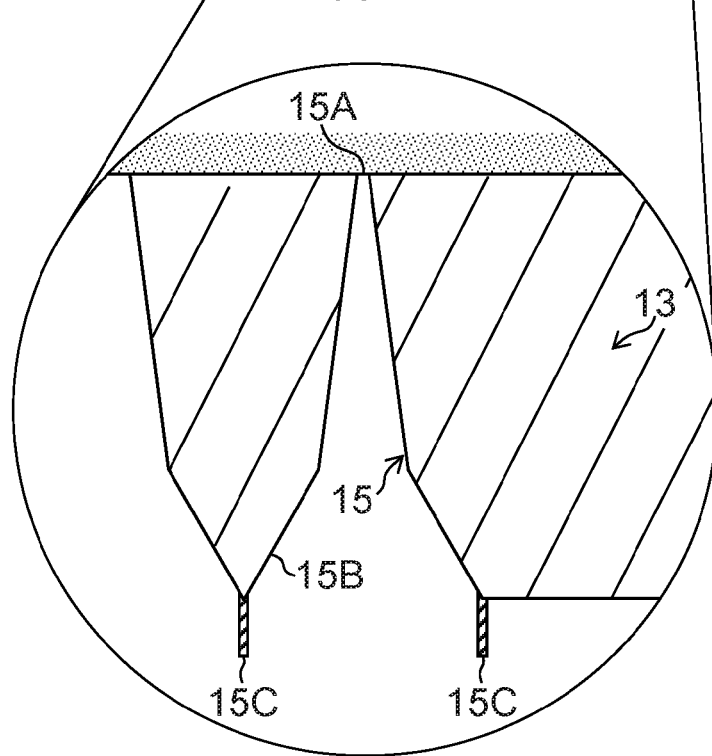

FIG. 7 is a diagram illustrating that enclosing members are formed on the microneedle structures. Portion (B) of FIG. 7 is an enlarged view of a portion enclosed by a circle in portion (A) of FIG. 7. As depicted in FIG. 7, the pressing surface of the mold 13 is preferably provided with enclosing members 15C that evenly partition the area of the transdermal absorption material to be fed into the adjacent needle-like recessed portions 15 into areas so that the enclosing members 15C project from the pressing surface. As depicted in FIG. 7, the enclosing members 15C are provided at the ends of the tapered portions 15B of the adjacent needle-like recessed portions 15, so as to project from the pressing surface. The amount by which the enclosing member 15C projects from the pressing surface needs to be smaller than the thickness of the two-layer film, and is preferably comparable to the thickness of an upper layer.

FIG. 7 depicts an example in which the enclosing members 15C are formed on the mold complex 14. However, this configuration is applicable to the normal mold 13 without the air vent hole 15A and the gas permeable sheet 16.

Additionally, more preferably, the mold 13 itself is formed of a raw material with high gas permeability. The oxygen permeability, which is representative of the gas permeability, of the mold 13 is preferably more than $1\times10^{-12}$ (mL/s·m²·Pa) and more preferably more than $1\times10^{-10}$ (mL/s·m²·Pa). Setting the gas permeability to within the above-described range allows the air present in the needle-like recessed portions 15 in the mold 13 to be removed from the needle-like recessed portions 15. This improves transferability to allow sharper microneedles 10 to be formed.

Examples of materials with the above-described gas permeability include a silicone resin (for example, Sylgard 184 (registered trademark) manufactured by Dow Corning Toray Co., Ltd. or KE-131OST (product number) manufactured by Shin-Etsu Chemical Co., Ltd.) a UV (ultraviolet) curing resin, and a plastic resin (for example, polystyrene or PMMA (polymethylmethacrylate) that is melted or dissolved into a solvent. Among these materials, silicone rubber containing raw materials can be suitably used because of the durability thereof against transfers based on repeated pressurization and the easiness of the peel-off thereof from the raw material. Furthermore, metallic raw materials include Ni, Cu, Cr, Mo, W, Ir, Tr, Fe, CO, MgO, Ti, Zr, Hf, V, Nb, Ta, α-aluminum oxide, zirconium oxide, stainless steel (for example, a STAVAX (trademark) material manufactured by Bohler-Uddeholm K K), and alloys thereof.

<Manufacture of the Transdermal Absorption Sheet>

Now, the manufacturing method for the transdermal absorption sheet 1 of the embodiment of the present invention is described with reference to FIGS. 8A to 8D.

FIGS. 8A to 8D depict a normal type of the mold 13. However, the above-described mold complex 14 is more preferably used.

(Preparation Steps for the Transdermal Absorption Material Solution)

A first transdermal absorption material solution 20A and a second transdermal absorption material solution 20B are prepared which are application solution to be applied onto a support 2 (hereinafter also referred to as a substrate) to form a two-layer film 20.

In the present embodiment, a multilayer film formed on the support 2 is described taking, as an example, the two-layer film 20 with an upper layer and a lower layer. However, the present invention is not limited to this number of layers. That is, on the support 2, the multilayer film may be formed which has a plurality of layers containing the transdermal absorption material and for which, when the lowermost layer is represented as a first layer, the uppermost layer is represented as a t-th layer (t≥2), and the viscosity of an n-th layer is represented as Vn, then V1>V2≥ ... ≥Vn≥ ... ≥Vt, at least one layer other than the lowermost layer containing a drug.

The first transdermal absorption material solution 20A is to be the lower layer in the two-layer film 20. The first transdermal absorption material solution 20A contains no drug and is adjusted to have a flowable viscosity. Furthermore, the second transdermal absorption material solution 20B is to be the upper layer in the two-layer film 20. The second transdermal absorption material solution 20B contains a drug and is adjusted to have a viscosity at which higher flowability can be achieved than in the first transdermal absorption material solution 20A in the lower layer.

In this regard, the flowabile viscosity refers to a viscosity at which the layers flow when, during the filling step described below, the mold 13 is pressed against the surface of the two-layer film 20 to apply a pressure to the surface.

The viscosity of the first transdermal absorption material solution 20A is preferably 200 Pa·s or more. Although the upper limit of the viscosity is not specified, because the first transdermal absorption material solution 20A needs to flow when pressed by the mold 13, the upper limit viscosity refers to the limit at which flowability can be achieved.

The viscosity of the second transdermal absorption material solution 20B is preferably 2 to 30 Pa·s. If the viscosity is 2 Pa·s, which corresponds to the lower limit viscosity, the second transdermal absorption material solution 20B flows when pressed by the mold 13, but does not flow and spread in the normal state.

The viscosity of the first transdermal absorption material solution 20A, which forms the lower layer, is preferably at least twice, more preferably at least five times, particularly preferably at least 10 times, and most preferably at least 20 times as high as the viscosity of the second transdermal absorption material solution 20B, which forms the upper layer. To achieve both coatability and flowability of the uppermost layer and the lowermost layer, the viscosity of the lowermost layer is preferably at most 1,000 times as high as the viscosity of the uppermost layer.

The support 2 is not limited as long as the support 2 is shaped like a thin film that can support the two-layer film 20. In particular, a relatively rigid plastic film such as PET (polyethylene terephthalate) or PEN (polyethylene naphthalate), a glass plate, paper, or the like may be used.

The first and second transdermal absorption materials are not limited to polymer materials, natural materials, or the like as long as the materials are polymer substances. However, the microneedles 10 of the transdermal absorption material enters the skin, and thus, in particular, water-soluble polymer substances are preferably used.

Preferably, the water-soluble polymer substance is any one of hydroxyethyl starch, dextran, chondroitin sulfate, hyaluronic acid, and carboxymethyl cellulose.

Furthermore, preferably, a biocompatible resin is used as a polymer material. It is preferable to use, as such a resin, sugar such as glucose, maltose, or pullulan, protein such as gelatin, polylactate, or a biodegradable polymer such as a lactic acid-glycollic acid copolymer. Among these resins, a gelatin containing raw material can tightly contact many supports 2 and has a high gel strength enough to allow the gelatin containing raw material to be used as a material that is gelled. Thus, the gelatin containing raw material can be suitably used during a peeling-off step described below because the raw material can be brought into tight contact with the support 2. The density of the resin is preferably such that 10 to 40% resin polymer is contained in the solution, though the density depends on the type of the material.

Additionally, a solvent used for dissolution may be other than hot water as long as the solvent has volatility, and alcohol may be used. A drug to be supplied to the inside of the human body may be dissolved into a solution of the polymer resin in accordance with an intended use.

Examples of a method for adjusting the viscosity of each layer include a method of selecting an appropriate polymer substance, a method of adjusting the content of a solvent in the polymer substance, and a method of mixing different polymer substances in an appropriate ratio.

Preferably, for a relatively low viscosity, hydroxyethyl starch, dextran, chondroitin sulfate, glucose, maltose, pullulan, gelatin, polylactate, lactic acid-glycollic acid copolymer, or the like is used as a transdermal absorption material contained in a low-viscosity layer, and a material obtained by adding a suitable amount of a high-viscosity polymer substance such as hyaluronic acid or carboxymethyl cellulose to the transdermal absorption material contained in the low-density layer is used as a transdermal absorption material contained in a high-viscosity layer.

The use of a transdermal absorption material with the above-described combination allows a transdermal absorption sheet with a drug concentrating at microneedles to be manufactured with high production efficiency.

More preferably, the transdermal absorption material forming the low-viscosity layer contains at least one selected from the group consisting of hydroxyethyl starch, dextran, and chondroitin sulfate, and the transdermal absorption material forming the high-viscosity layer contains at least one selected from the group consisting of hydroxyethyl starch, dextran, and chondroitin sulfate and at least one selected from the group consisting of hyaluronic acid and carboxymethyl cellulose.

Preferably 50 wt % or more, more preferably 0 wt % or more, and much more preferably 90 wt % or more of the transdermal absorption material forming the low-viscosity layer is a polymer substance selected from the group consisting of hydroxyethyl starch, dextran, and chondroitin sulfate. Preferably 50 wt % or more, more preferably 80 wt % or more, and much more preferably 90 wt % or more of the transdermal absorption material forming the high-viscosity layer is a polymer substance selected from the group consisting of hydroxyethyl starch, dextran, chondroitin sulfate, hyaluronic acid, and carboxymethyl cellulose.

Furthermore, when the tip of each needle-like protruding portion in the transdermal absorption sheet contains: drug; and at least one selected from the group consisting of hydroxyethyl starch, dextran and chondroitin sulfate, and the base of the needle-like protruding portion in the transdermal absorption sheet contains: at least one selected from the group consisting of hydroxyethyl starch, dextran and chondroitin sulfate; and at least one selected from the group consisting of hyaluronic acid and carboxymethyl cellulose, the transdermal absorption sheet has high drug utilization efficiency and is hard to break. Preferably, the tip of the needle-like protruding portion contains hydroxyethyl starch, and the base of the needle-like protruding portion contains hydroxyethyl starch and hyaluronic acid.

In the transdermal absorption sheet, preferably 50 wt % or more, more preferably 80 wt % or more, and much more preferably 90 wt % or more of the transdermal absorption material forming the tip of the needle-like protruding portion is a polymer substance selected from the group consisting of hydroxyethyl starch, dextran, and chondroitin sulfate. In the transdermal absorption sheet, preferably 50 wt % or more, more preferably 80 wt % or more, and much more preferably 90 wt % or more of the transdermal absorption material forming the base of the needle-like protruding portion is a polymer substance selected from the group consisting of hydroxyethyl starch, dextran, chondroitin sulfate, hyaluronic acid, and carboxymethyl cellulose.

Furthermore, the drug contained in the second transdermal absorption material solution 20B is not limited as long as the drug accomplishes the functions of the drug, but is particularly preferably selected from the group consisting of peptide, protein, nucleic acid, polysaccharide, a vaccine, a medical compound belonging to a water-soluble low-molecular-weight compound, or a cosmetic component.

Additionally, as the water-soluble polymer substance contained in the second transdermal absorption material solution 20B, one that does not interact with the drug contained is preferably used. For example, if protein is used as the drug, when a chargeable polymer substance is mixed with the protein, the protein and the polymer substance electrostatically interact with each other to form an aggregate, which is cohered and precipitated. Therefore, when a chargeable substance is used in the drug, a water-soluble polymer substance with no charge such as hydroxyethyl starch or dextran is preferably used.

For a method for preparing the second transdermal absorption material solution 20B, when a water-soluble polymer (gelatin or the like) is used for example, the second transdermal absorption material solution 20B can be manufactured by dissolving water-soluble powder into water, and after the dissolution, adding a medicine to the solution. If the material is difficult to dissolve into water, the material may be dissolved on heating. The temperature may be selected as needed depending on the type of the polymer material, but the material is preferably heated at approximately 60° C. (laminating step).

Figure 8A:
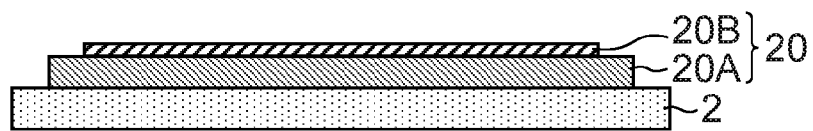
FIG. 8A is a diagram illustrating a manufacturing method for a transdermal absorption sheet according to the embodiment of the present invention.

As depicted in FIG. 8A, the first transdermal absorption material solution 20A with a high viscosity is applied onto the support 2 to form a lower layer, and the second transdermal absorption material solution 20B with a low viscosity is applied onto the lower layer to form an upper layer. Thus, the two-layer film 20 consisting of the lower layer with the high viscosity and the upper layer with the low viscosity and having a viscosity difference is laminated on the support 2. In this case, for the upper layer formed of the second transdermal absorption material solution 20B, the needed coating amount, that is, the needed coating thickness, of the second transdermal absorption material solution 20B is set based on the post-molding set solids amount of the microneedles 10 to be molded and the solids concentration of the second transdermal absorption material solution 20B.

That is, for one unit of the needle-like recessed portion 15, the needed coating amount per needle-like recessed portion is calculated from a set value for the solids amount (for example, the material is solidified by means of drying or the like up to a moisture amount at which the microneedles 10 have elasticity) of the second transdermal absorption material 20B to be fed into the needle-like recessed portion 15 and the solids concentration of the second transdermal absorption material solution 20B prepared in the preparing step for the transdermal absorption material. Then, the layer thickness of the upper layer is calculated by dividing a total coating amount resulting from multiplication of the coating amount per needle-like recessed portion by the number of needle-like recessed portions 15 formed in the mold 13, by the size of the area of the two-layer film 20 which is pressed against the mold 13. In this regard, the calculation for the size of the area pressed may be executed on the assumption that the mold 13 has no needle-like recessed portion and is flat.

The applied film thickness of the first transdermal absorption material solution 20A forming the lower layer is not particularly limited but is preferably approximately 300 to 500 μm because an excessively large thickness makes the transdermal absorption material useless.

A coater that applies the first and second transdermal absorption material solutions 20A and 20B is not particularly limited, but metering coaters such as a slot coater, a rod coater, a knife coater, and a gravure coater which facilitate application of a given amount are preferred because the second transdermal absorption material solution 20B needs to be applied so as to achieve an accurate coating thickness.

For the above-described laminating step, besides the basic aspect in which the two-layer film 20 is formed by applying the lower layer onto the support 2 and applying the upper layer onto the lower layer, the following aspects may be carried out.

<Aspect 1> A method of applying the first transdermal absorption material solution 20A onto the support 2 to form the lower layer, then temporarily drying the lower layer, and applying the second transdermal absorption material solution 20B to the dried lower layer to form the upper layer.

<Aspect 2> A method of applying the first transdermal absorption material solution 20A onto the support 2 to form the lower layer, then temporarily drying the lower layer, applying the second transdermal absorption material solution 20B to the dried lower layer to form the upper layer, then temporarily drying the upper layer, and then allowing the resultant structure to absorb water to form the two-layer film 20.

<Aspect 3> A method of applying the first transdermal absorption material solution 20A onto the support 2 and drying the first transdermal absorption material solution 20A to form the lower layer, while applying the second transdermal absorption material solution 20B onto the support 2 and drying the second transdermal absorption material solution 20B to form the lower layer, peeling the upper layer off from the support 2 and laminating the upper layer to the lower layer, and then allowing the resultant structure to absorb water to form the two-layer film 20.

In Aspects 1 to 3, the drying of the upper layer and the lower layer is preferably preformed such that the water content of the layers is 20 wt % or less.

(Filling Step)

Figure 8B:
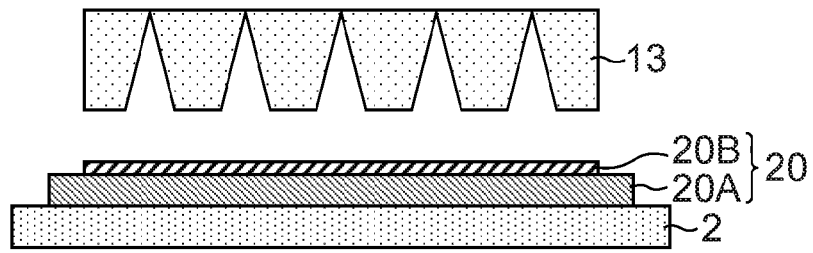
FIG. 8B is a diagram illustrating the manufacturing method for the transdermal absorption sheet according to the embodiment of the present invention.
Figure 8C:
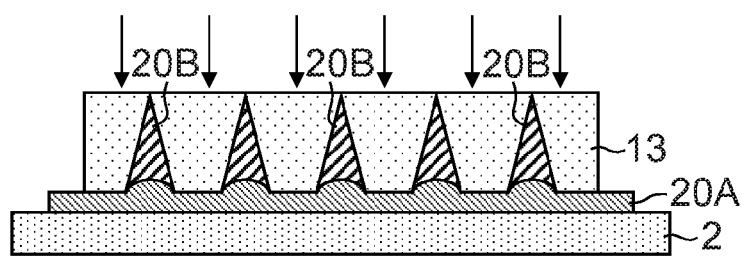
FIG. 8C is a diagram illustrating the manufacturing method for the transdermal absorption sheet according to the embodiment of the present invention.

As depicted in FIGS. 8B and 8C, the needle-like recessed portions 15 are filled with the transdermal absorption material by pressing the mold 13 produced as described above against the surface of the two-layer film 20 supported by the support 2 to allow the two-layer film 20 to flow.

In such a filling step, the first transdermal absorption material solution 20A forming the lower layer and the second transdermal absorption material solution 20B forming the upper layer have a viscosity difference and thus flows in a manner described below.

Figure 9A:
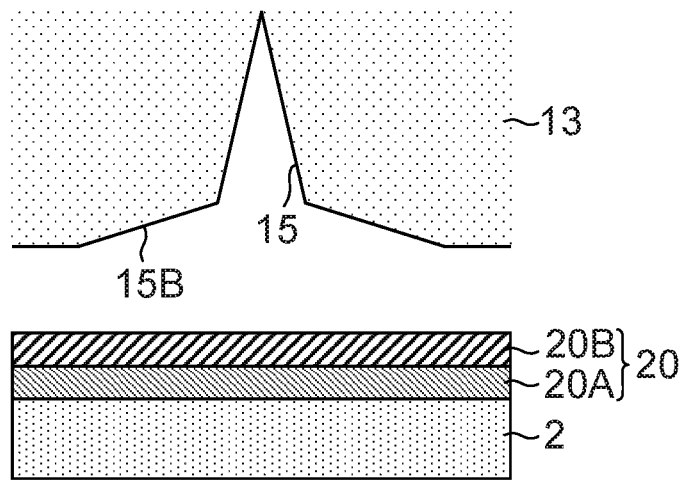
FIG. 9A is a diagram illustrating motion of a transdermal absorption material in a filling step in the embodiment of the present invention.
Figure 9B:
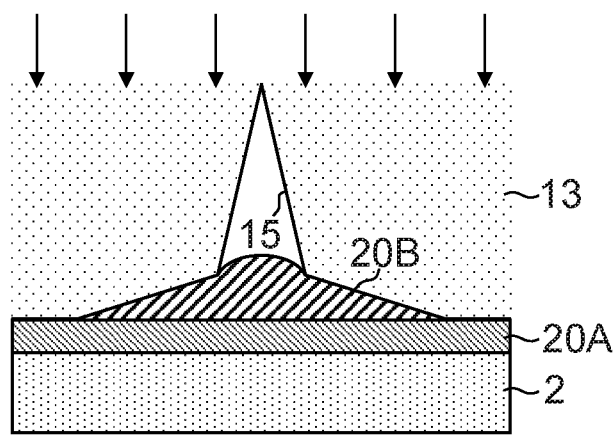
FIG. 9B is a diagram illustrating the motion of the transdermal absorption material in the filling step in the embodiment of the present invention.

As depicted in FIG. 9A, the mold 13 is positioned above the two-layer film 20 formed on the support 2. Then, as depicted in FIG. 9B, the mold 13 is pressed against the surface of the two-layer film 20. Thus, since the upper layer in the two-layer film 20 has a lower viscosity than the lower layer in the two-layer film 20, first, the second transdermal absorption material solution 20B with the lower viscosity in the upper layer flows into the needle-like recessed portions 15. Thus, the needle-like recessed portions 15 in the mold 13 are each filled only with the second transdermal absorption material solution 20B with the lower viscosity, but not filled up to the tip of the needle-like recessed portions 15.

Figure 9C:
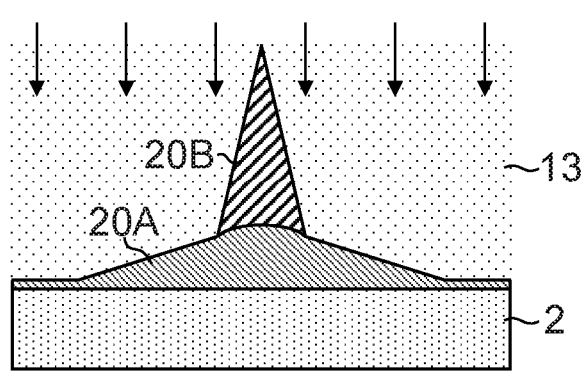
FIG. 9C is a diagram illustrating the motion of the transdermal absorption material in the filling step in the embodiment of the present invention.

As depicted in FIG. 9C, the mold 13 is further continuously pressed against the surface of the two-layer film 20, the first transdermal absorption material solution 20A in the lower layer, having a next higher viscosity than in the upper layer, acts to flow into the needle-like recessed portions 15. Thus, the second transdermal absorption material solution 20B already contained in the needle-like recessed portions 15 is pushed toward the tip side of each needle-like recessed portion 15.

Therefore, in the laminating step, when the layer thickness of the upper layer is set based on the solids amount of the microneedles 10 and the solids concentration of the second transdermal absorption material solution 20B, an approximately total amount of second transdermal absorption material solution 20B containing the drug is filled into the needle-like recessed portions 15. As a result, the drug can be concentrated at the microneedles 10 on the molded transdermal absorption sheet 1.

The pressure at which the mold 13 is pressed against the surface of the two-layer film 20 is preferably the pressure at which mold 13 can be displaced at a constant speed of 10 to 2,000 µm/min toward the support 2.

When the speed of the displacement exceeds 2,000 µm/min, the second transdermal absorption material solution 20B in the upper layer flows and escapes out of the needle-like recessed portions 15 before the second transdermal absorption material solution 20B in the upper layer is completely filled into the needle-like recessed portions 15. Furthermore, when the speed of the displacement is less than 10 µm/min, the filling step has a prolonged duration, reducing production efficiency.

Additionally, when the duration of the filling step is to be shortened, the mold 13 can be pressed against the two-layer film 20 so as to be displaced toward the support 2 while being gradually accelerated within a speed range of 10 to 2,000 µm/min.

Many of the drugs used have the risk of being thermally decomposed, and thus, the laminating step, the filling step, and the peeling-off step in the present embodiment are preferably executed at normal temperature. Furthermore, also when the solidifying step is executed by means of drying, drying temperature is preferably low enough to prevent the drug from being decomposed.

Figure 10A:
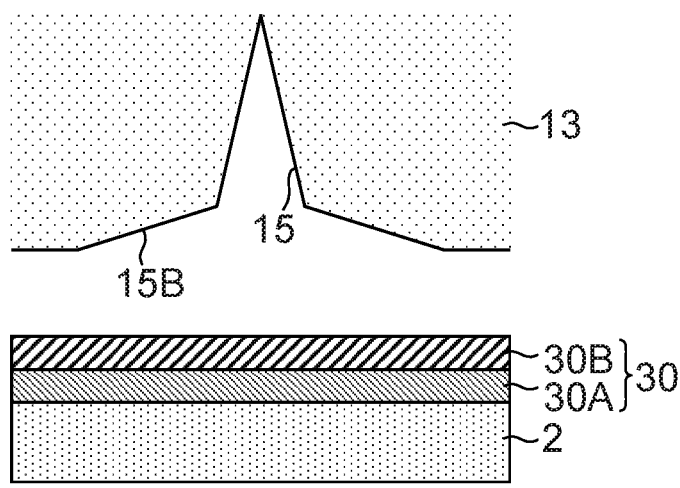
FIG. 10A is a diagram illustrating the motion of the transdermal absorption material observed when the viscosity of an upper layer is the same as the viscosity of a lower layer.
Figure 10B:
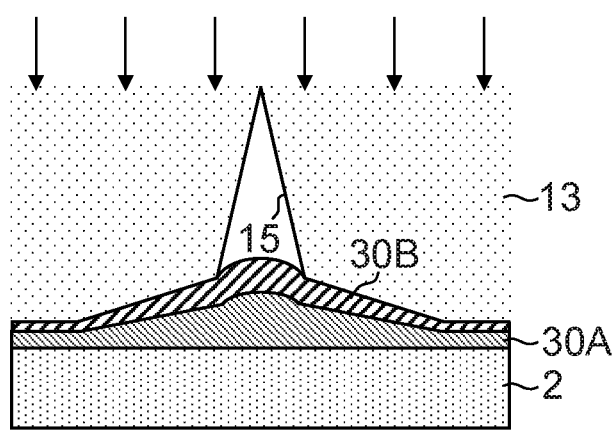
FIG. 10B is a diagram illustrating the motion of the transdermal absorption material observed when the viscosity of the upper layer is the same as the viscosity of the lower layer.
Figure 10C:
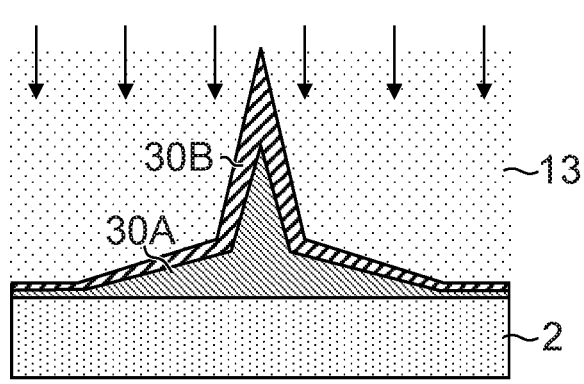
FIG. 10C is a diagram illustrating the motion of the transdermal absorption material observed when the viscosity of the upper layer is the same as the viscosity of the lower layer.

FIGS. 10A to 10C are comparative diagrams illustrating the embodiment of the present invention and depicting motion of the transdermal absorption material observed when a lower layer 30A and an upper layer 30B forming a two-layer film 20 have the same viscosity.

As depicted in FIG. 10A, the mold 13 is positioned above the two-layer film 20, and as depicted in FIG. 10B, the mold 13 is pressed against the surface of the two-layer film 30 supported by the support 2. The pressure at which the mold 13 is pressed against the two-layer film 20 is similar to the pressure in the embodiment of the present invention depicted in FIG. 9B.

However, as seen in FIG. 10B, when the lower layer 30A and the upper layer 30B have the same viscosity, pressing the mold 13 causes the lower layer 30A and the upper layer 30B to start flowing at the same time. Thus, as depicted in FIG. 10C, the needle-like recessed portions 15 are filled with the lower layer 30A and the upper layer 30B in a state where the two-layer film 30 is retained. That is, a portion of the upper layer 30B is filled into a wall surface side of each needle-like recessed portion 15, and a portion of the lower layer 30A is filled into a central portion side of the needle-like recessed portion 15 so as to be enveloped by a portion of the upper layer 30B.

Thus, when the lower layer 30A and the upper layer 30B has the same viscosity, the drug cannot be concentrated at the microneedle 10 of the molded transdermal absorption sheet 1.

<Solidifying Step>

In the solidifying step, the two-layer film 20 is solidified with the mold 13 kept pressed against the surface of the two-layer film 20, that is, in a state depicted in FIG. 8C. Strictly speaking, the transdermal absorption materials having formed the two-layer film 20 is solidified in the solidification step because the upper layer is filled into the needle-like recessed portion 15 so that the inside of the needle-like recessed portion 15 is not in the two-layer film state. However, for simplification, the solidification is referred to as a solidification of the two-layer film.

As a method for the solidification, drying solidification can be suitably performed.

In a method for drying solidification, warm air is blown against th two-layer film. The warm air is preferably dehumidified and has a temperature of 35° C. and a relative humidity of 50% or less, and more preferably 10% or less, for example. When warm air at high temperature is flown for drying, an excessively high temperature of the warm air may cause, depending on the type of a medicine used, for example, decomposition of the medicine on heating, leading to a change in the efficacy of the medicine. Thus, care needs to be taken for the temperature of the blown warm air.

The solidified transdermal absorption material solution causes the transdermal absorption material to be contracted more significantly than in the case of filling the transdermal absorption material into the needle-like recessed portions 15, facilitating peel-off of the transdermal absorption material from the mold 13. Furthermore, in the drying solidification, an excessively low moisture amount of the transdermal absorption material makes peel-off difficult, and thus, the moisture amount at which elasticity is kept is preferably maintained. Specifically, drying is preferably stopped when the moisture amount is 10 to 20%, though the moisture amount depends on the type of the transdermal absorption material forming the microneedle 10.

(Peeling-off Step)

Figure 8D:
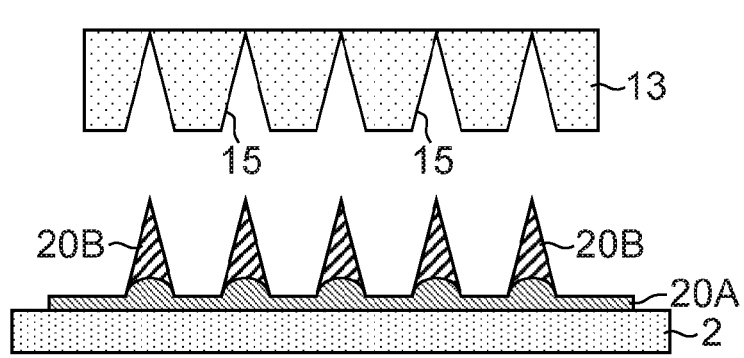
FIG. 8D is a diagram illustrating the manufacturing method for the transdermal absorption sheet according to the embodiment of the present invention.
Figure 11A:
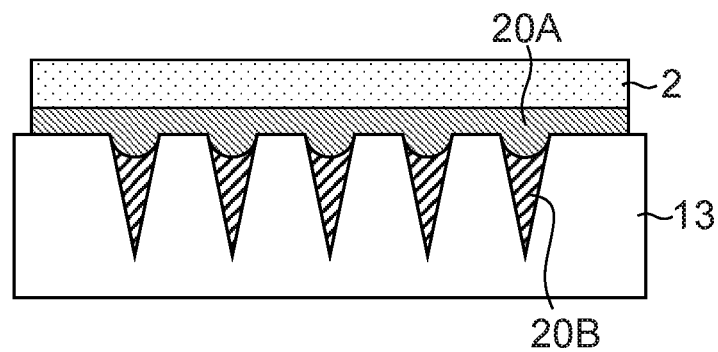
FIG. 11A is a diagram illustrating a peeling-off step.
Figure 11B:
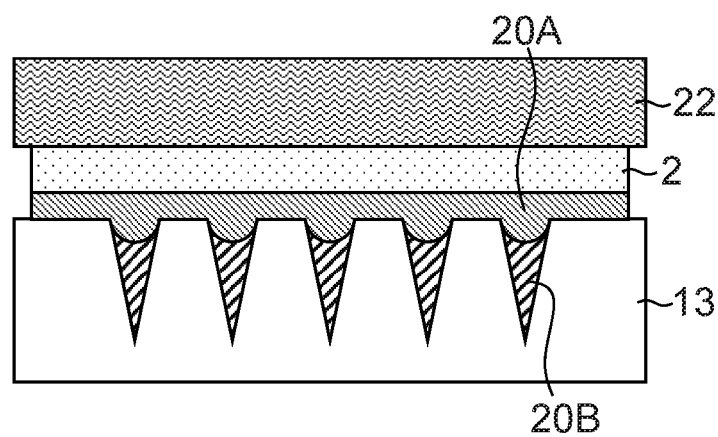
FIG. 11B is a diagram illustrating the peeling-off step.

As depicted in FIG. 8D, in the peeling-off step, the solidified two-layer film 20 supported by the support 2 is peeled off from the mold 13. Specifically, as depicted in FIG. 11A, the mold 13 is poisoned on the lower side, and the support 2 supporting the two-layer film 20 is positioned on the upper side. Then, as depicted in FIG. 11B, a peel-off sheet 22 with an adhesive layer formed thereon is attached to the support 2. For example, a PET film may be adopted as the material peel-off sheet 22.

Figure 11C:
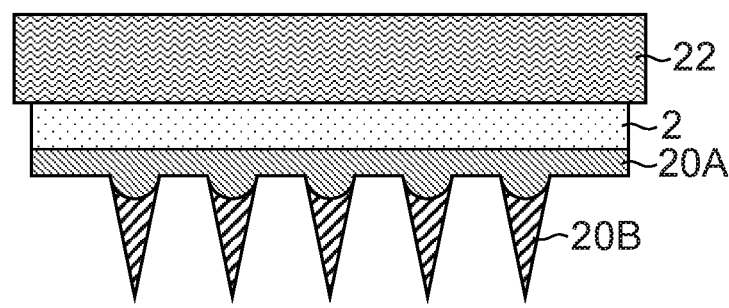
FIG. 11C is a diagram illustrating the peeling-off step.

Then, the two-layer film 20 is peeled off from the mold 13 by flipping the peel-off sheet 22 up at an end thereof. Thus, a transdermal absorption sheet in a state where the peel-off sheet 22 is attached thereon is manufactured as depicted in FIG. 11C, and subsequently, the peel-off sheet 22 is peeled off from the support 2. As a result, the transdermal absorption sheet 1 is manufactured.

Furthermore, as another aspect of the peeling-off method, a method, though not depicted in the drawings, is available which involves: attaching a plurality of suckers to the support 2, sucking an air so that the suckers adsorb onto the support 2, and pulling the suckers to peel off the two-layer film 20.

The peeing-off step of peeling the solidified two-layer film 20 off from the mold 13 is an important step. Normally, as in the embodiment, when a structure with the microneedles 10 with a high aspect ratio is peeled off from the mold 13, the large contact area of the microneedles 10 causes high stress to be exerted on the microneedles 10, which are thus destroyed. The microneedles 10 then remain in the needle-like recessed portions 15 of the mold 13 instead of being peeled off from the mold 13. Thus, the resultant transdermal absorption sheet 1 has fatal defects.

Based on this, in the present embodiment, the material constituting. the mold 13 is preferably composed of a material that significantly facilitates peel-off. Furthermore, when the material constituting the mold 13 is a high-elastic soft material, the stress exerted on the microneedles 10 can be relaxed at the time of peel-off.

Additionally, to allow evaporation of moisture remaining in the microneedles 10 on the surface of the transdermal absorption sheet 1, dry air may be blown against the microneedles 10 or vacuum drying may be performed on the microneedles 10, after peel-off. Specifically, immediately before packing, the moisture amount of the transdermal absorption sheet 1 is set to 10% or less, and desirably 5% or less. Alternatively, the transdermal absorption sheet 1 may be packed together with a drying material so as to set the moisture amount of the transdermal absorption sheet 1 to 10% or less, and desirably 5% or less, after packing.

EXAMPLES

Specific examples of the manufacturing method for the transdermal absorption sheet 1 in the present invention are described below.

Test 1

Test 1 involved determining how the rate of the drug concentrated at the microneedles 10 (filling rate) varied between cases where the conditions for the manufacturing method for the transdermal absorption sheet 1 according to the embodiment of the present invention were met and cases where the conditions were not met.

<Production of the Mold>

Figure 12A:
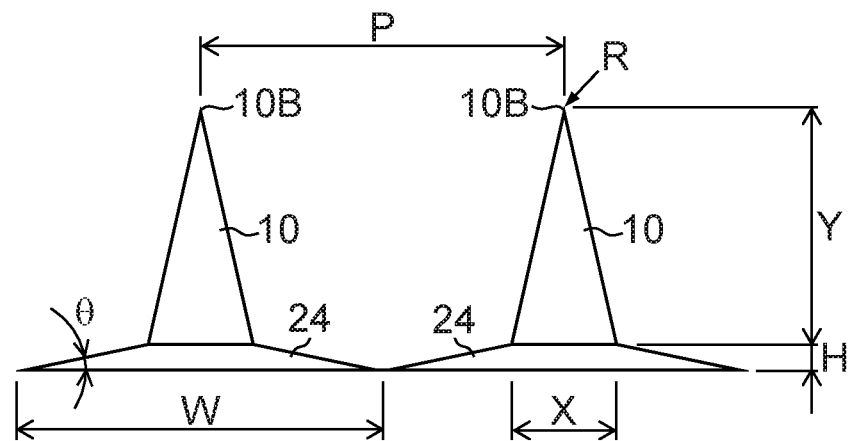
FIG. 12A is a side view of microneedles (projecting shapes) on a transdermal absorption sheet manufactured in an example.
Figure 12B:
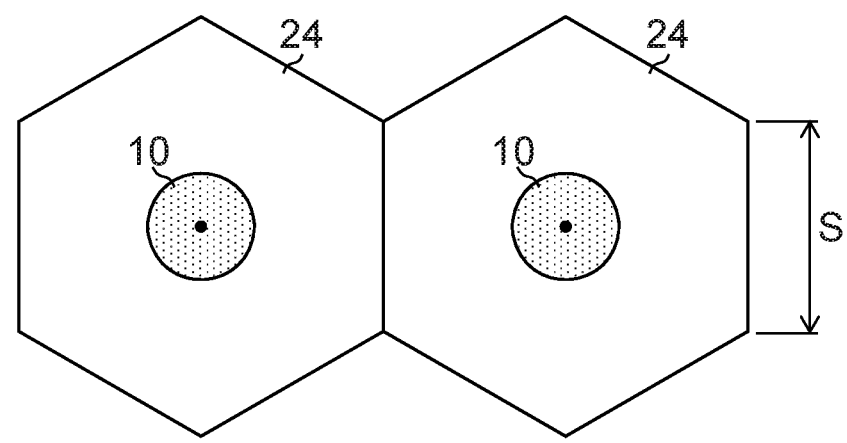
FIG. 12B is a top view of the microneedles (projecting shapes) on the transdermal absorption sheet manufactured in the example.

FIGS. 12A and 12B depict the projecting shape of the transdermal absorption sheet 1 manufactured. FIG. 12A is a side view, and FIG. 12B is a top view.

As depicted in FIGS. 12A and 12B, the projecting shape is such that a conical microneedle 10 (needle-like protruding portion) with a bottom surface diameter X of 420 μm and a height Y of 700 μm is loaded on a hexagonal truncated pyramid 24. The hexagonal truncated pyramid 24 has: a hexagonal bottom surface with a length of 404 μm on one side S and a diameter W of 700 μm, a circular top surface with a diameter of 420 μm, and a height H of 420 μm.

The hexagonal pyramid 24 corresponds to the tapered portion 15B of the mold 13.

The pitch P between the microneedle 10 and the microneedle 10 was set to 700 μm, and the radius of curvature R of the microneedle tip 10B was set to at most 5 μm. Furthermore, the taper angle θ of the hexagonal pyramid 24 was set to 16.7°.

The original plate 11 was produced by forming, by means of grinding, 37 projecting shapes as described above in a honeycomb array depicted in FIG. 6 on a surface of a flat Ni plate of a length of 40 mm on one side.

Then, on the original plate 11, silicone rubber (SILASTIC (trademark), MDX4-4210 (product number) manufactured by Dow Corning Toray Co., Ltd.) was formed into a film of thickness of 692 μm. The film was thermally cured with the microneedle tips of the original plate 11 projecting from a film surface by 50 μm, and then peeled off. Thus, an inverted article of silicone rubber with air vent holes (through-holes) of diameter of approximately 30 μm was produced. The 37 needle-like recessed portions 15, which are inverted shapes of the above-described projecting shapes, are arranged in a central area of the inverted article in a honeycomb structure. The central area corresponds to the pressing surface to be pressed against the two-layer film. Thus, the mold 13 with a diameter of 5 mm was produced by cutting off the entire area of the inverted article other than the central area. Then, the mold complex 14 was formed by laminating the gas permeable sheet to the back surface of the mold 13.

Example 1

<Preparation of the Transdermal Absorption Material Solution>

The first transdermal absorption material solution 20A forming the lower layer was prepared as a mixed water solution resulting from mixture of a water solution with a hydroxyethyl starch (molecular weight of 70,000; manufactured by Fresenius Kabi) concentration of 39 wt % and a water solution with a sodium hyaluronate (molecular) weight of 900,000 to 1,050,000; manufactured by Maruha Nichiro Corporation) concentration of 1 wt %.

Furthermore, the second transdermal absorption material solution 20B forming the upper layer was prepared as mixed solution which contained a water solution with a hydroxyethyl starch concentration of 14 wt % and in which 0.25 wt % human growth hormone (growth hormone, human, recombinant, for biochemistry; manufactured by Wako Pure Chemical Industries, Ltd.) was contained as a drug and FITC (fluoroscein isothiocyanate: manufactured by PD Research, FACS-D1 (product number)), which is a type of fluorescent dye, was also contained so as to have an FITC concentration of 0.001 wt %.

<Laminating Step>

The first transdermal absorption material solution 20A prepared as described above was applied onto the support 2 to a thickness of approximately 300 μm and dried at 35° C. and at a relative humidity of 40% to form a lower layer with a high viscosity. A glass plate was used as the support 2, and this also applied to the other examples. Subsequently, the second transdermal absorption material solution 20B prepared as described above was applied onto the lower layer to a thickness of 110 μm form an upper layer of a low viscosity. Thus, the two-layer film 20 with a viscosity difference was formed on the support 2.

The following method was used as an evaluation method for the viscosity in the layer state of the lower layer and the upper layer. First, immediately before the filling step, the lower layer and the upper layer are focused on by means of micro-Raman spectroscopy. The signal ratio between CH groups and OH groups in the corresponding site was measured for each of the lower and upper layers. The focus is determined by predicting the positions of the upper layer and the lower layer based on distances from the uppermost surface. Then, the water content of the lower layer is calculated by determining the water content at the measured signal ratio based on a standard line indicative of the relation between the water content of the substance in the same composition as that of a pre-produced lower layer and the signal ratio of CH groups and OH groups. Then, the viscosity of the lower layer is obtained by measuring the viscosity, at the calculated water content, of the substance in the same composition as that of the lower layer (The Bohlin Gemini HR nano Reometer System manufactured by Malvern Instruments Ltd.). The viscosity value of the upper layer is calculated in a manner similar to the manner for the lower layer.

The viscosity of the high-viscosity lower layer determined using the above-described evaluation method was 1,000 Pa·s. The viscosity of the low-viscosity upper layer determined using the above-described evaluation method was 2 Pa·s. The lower layer had a viscosity 500 times higher than the viscosity of the upper layer.

<Filling Step>

Immediately after the formation of the two-layer film 20 on the support 2 by means of coating, the mold 13 produced as described above was brought into tight contact with the surface of the two-layer film 20. The mold 13 was pressed toward the support 2 so as to be displaced at a constant speed of 200 μm/min, thus filling the inside of each needle-like recessed portion 15 of the mold 13 with the transdermal absorption material. Once the needle-like recessed portion 15 was completely filled with the transdermal absorption material, the pressing of the mold 13 was stopped.

<Solidifying Step and Peeling-off Step for the Two-layer Film>

While a pressure of 10 g/cm² was being applied to the two-layer film 20 through the upper surface of the mold 13, the two-layer film 20 was solidified by being dried at 35° C. and at a relative humidity of 40%. Subsequently, the transdermal absorption sheet 1 was produced by peeling the mold 13 off from the two-layer film.

Example 2

In Example 2, the transdermal absorption sheet 1 was produced under conditions similar to the conditions for Example 1 except for the composition of the first transdermal absorption material solution 20A for forming the lower layer.

That is, a mixed water solution with a hydroxyethyl starch concentration of 39.5 wt % and a sodium hyaluronate concentration of 0.5 wt % was applied onto the support to a thickness of approximately 300 μm and dried at 35° C. and at a relative humidity of 40% to form the lower layer. Subsequently, the second transdermal absorption material solution 20B with the same composition as that in Example 1 was applied onto the lower layer to a thickness of 110 μm form the upper layer. Thus, the two-layer film 20 was formed. The viscosity of the lower layer produced as described above was 200 Pa·s. The viscosity of the upper layer produced as described above was 2 Pa·s. The lower layer had a viscosity 100 times higher than the viscosity of the upper layer.

Example 3

In Example 3, the transdermal absorption sheet 1 was produced under conditions similar to the conditions for Example 1 except for the composition of the first transdermal absorption material solution 20A for forming the lower layer.

That is, a mixed water solution with a hydroxyethyl starch concentration of 39.75 wt % and a sodium hyaluronate concentration of 0.25 wt % was applied onto the support 2 to a thickness of approximately 300 μm and dried at 35° C. and at a relative humidity of 40% to form the lower layer. Subsequently, the second transdermal absorption material solution 20B with the same composition as that in Example 1 was applied onto the lower layer to a thickness of 110 μm form the upper layer. Thus, the two-layer film 20 was formed. The viscosity of the lower layer produced as described above was 10 Pa·s. The viscosity of the upper layer produced as described above was 2 Pa·s. The lower layer had a viscosity five times higher than the viscosity of the upper layer.

Example 4

In Example 4, the transdermal absorption sheet 1 was produced under conditions similar to the conditions for Example 1 except that the composition of the second transdermal absorption material solution 20B for forming the upper layer was changed from the composition in Example 1.

That is, the same first transdermal absorption material solution 20A as that in Example 1 was applied onto the support 2 to a thickness of approximately 300 μm and dried at 35° C. and at a relative humidity of 40% to form the lower layer. A mixed solution was prepared by adding human growth hormone as a drug and FITC, to a mixed water solution with a hydroxyethyl starch concentration of 13.9 wt % and a sodium hyaluronate concentration of 0.1 wt %, so as to have a human growth hormone concentration of 0.25 wt % and an FITC concentration of 0.001 wt %. Subsequently, the surface of the lower layer was coated with the prepared mixed solution to a thickness of 110 μm. Thus, the two-layer film 20 was formed on the support 2. The viscosity of the lower layer produced as described above was 1,000 Pa·s. The viscosity of the upper layer produced as described above was 30 Pa·s. The lower layer had a viscosity 33 times higher than the viscosity of the upper layer.

Example 5

In Example 5, the transdermal absorption sheet 1 was produced under conditions similar to the conditions for Example 1 except that the composition of the first transdermal absorption material solution 20A for forming the lower layer and the composition of the second transdermal absorption material solution 20B for forming the upper layer were changed from the compositions in Example 1.

That is, a water solution with a hydroxyethyl starch concentration of 40 wt % was applied onto the support 2 to a thickness of approximately 300 μm and dried at 35° C. and at a relative humidity of 40% to form the lower layer. A mixed solution was prepared by adding BSA (Albumin, from bovine serum manufactured by SIGMA Corporation) as a drug and FITC, to a water solution with a sodium chondroitin sulfate (sodium chondroitin sulfate specified in Japanese Pharmaceutical Codex; manufactured by Maruha Nichiro Corporation) concentration of 14 wt %, so as to have a BSA concentration of 0.25 wt % and an FITC concentration of 0.001 wt %. Subsequently, the surface of the lower layer was coated with the prepared mixed solution to a thickness of 110 μm. Thus, the two-layer film 20 was formed on the support 2. The viscosity of the lower layer produced as described above was 200 Pa·s. The viscosity of the upper layer produced as described above was 10 Pa·s. The lower layer had a viscosity 20 times higher than the viscosity of the upper layer.

Example 6

In Example 6, the composition of the first transdermal absorption material solution 20A for forming the lower layer and the composition of the second transdermal absorption material solution 20B for forming the upper layer were changed from the compositions in Example 1, and the lower layer that had not been dried was coated with the upper layer. Furthermore, the layer thicknesses of the lower layer and the upper layer were changed. As to the other conditions, the transdermal absorption sheet 1 was produced under conditions similar to Example 1.

That is, a mixed water solution with a hydroxyethyl starch concentration of 48.8 wt % and a sodium hyaluronate concentration of 1.2 wt % was applied onto the support 2 to a thickness of approximately 240 μm to form the lower layer. A mixed solution was prepared by adding human growth hormone as a drug and FITC, to a water solution with a hydroxyethyl starch concentration of 50 wt % so as to have a human growth hormone concentration of 0.25 wt % and an FITC concentration of 0.001 wt %. Subsequently, the upper layer was formed by coating the surface of the lower layer that had not been dried with the prepared mixed solution to a thickness of 15 μm. Thus, the two-layer film 20 was formed on the support 2. The viscosity of the lower layer produced as described above was 1,000 Pa·s, The viscosity of the upper layer produced as described above was 2 Pa·s. The lower layer had a viscosity 500 times higher than the viscosity of the upper layer.

Example 7

In Example 7, the compositions of the lower layer and the upper layer were similar to the compositions in Example 1, but the two-layer film was formed by applying the upper layer, then drying the upper layer and further applying water to the upper layer for humidification. As to the other conditions, the transdermal absorption sheet 1 was produced under conditions similar to Example 1.

That is, the same first transdermal absorption material solution 20A as that in Example 1 was applied onto the support 2 to a thickness of approximately 300 μm and dried at 35° C. and at a relative humidity of 40% to form the lower layer. Subsequently, the same second transdermal absorption material solution 20B as that in Example 1 was applied onto the lower layer to a thickness of 110 μm and dried at 35° C. and at a relative humidity of 40% to form the upper layer. Then, water was applied onto the upper layer to a thickness of 100 μm for humidification. Thus, the two-layer film 20 was formed on the support 2. The viscosity of the lower layer produced as described above was 1,000 Pa·s. The viscosity of the upper layer produced as described above was 2 Pa·s. The lower layer had a viscosity 500 times higher than the viscosity of the upper layer.

Example 8

In Example 8, the compositions of the lower layer and the upper layer were similar to the compositions in Example 1. However, the lower layer and the upper layer were separately applied onto the support 2 and dried, and then, the upper layer was peeled off from the support 2 and laminated to the lower layer, and water was applied for humidification. The two-layer film 20 was thus formed. As to the other conditions, the transdermal absorption sheet 1 was produced under conditions similar to Example 1.

That is, the same first transdermal absorption material solution 20A as that in Example 1 was applied onto the support 2 to a thickness of approximately 300 μm and dried at 35° C. and at a relative humidity of 40% to form the lower layer. Furthermore, the same second transdermal absorption material solution 20B as that in Example 1 was applied onto the support 2 to a thickness of 110 μm and dried at 35° C. and at a relative humidity of 40% to form the upper layer.

The upper layer was peeled off from the support 2 and laminated to the lower layer so as to tightly contact with the lower layer, and then, water was applied onto the upper layer to a thickness of 100 μm to form the two-layer film 20. The viscosity of the lower layer produced as described above was 1,000 Pa·s, The viscosity of the upper layer produced as described above was 2 Pa·s. The lower layer had a viscosity 500 times higher than the viscosity of the upper layer.

Example 9

In Example 9, the compositions of the lower layer and the upper layer were similar to the compositions in Example 1. However, the two-layer film was formed by applying the upper layer onto the lower layer applied onto the support 2 without drying the lower layer. Furthermore, a displacement speed at which the mold 13 was pressed against the two-layer film 20 was changed from the displacement speed in Examples 1 to 8. As to the other conditions, the transdermal absorption sheet 1 was produced under conditions similar to Example 1.

That is, the same first transdermal absorption material solution 20A as that in Example 1 was applied onto the support 2 to a thickness of approximately 300 μm to form the lower layer. Subsequently, the same second transdermal absorption material solution 20B as that in Example 1 was applied onto the lower layer to a thickness of 110 μm to form the upper layer. Thus, the two-layer film 20 was formed on the support 2. The viscosity of the lower layer produced as described above was 1,000 Pa·s. The viscosity of the upper layer produced as described above was 2 Pa·s. The lower layer had a viscosity 500 times higher than the viscosity of the upper layer.

The mold 13 was brought into tight contact with the surface of the two-layer film 20 formed as described above. The mold 13 was pressed toward the support 2 while being accelerated over 30 seconds at a displacement speed from 10 μm/min to 200 μm/min, to fill the needle-like recessed portions 15 in the mold 13 with the transdermal absorption material. The displacement of the mold 13 was stopped when the needle-like recessed portions 15 were completely filled with the transdermal absorption material.

Comparative Example 1

Comparative Example 1 is a case where the transdermal absorption sheet 1 was produced with the same viscosity set for the lower layer and the upper layer.

That is, a water solution with a hydroxyethyl starch concentration of 40 wt % was applied onto the support 2 to a thickness of approximately 300 μm and dried at 35° C. and at a relative humidity of 40% to form the lower layer. Subsequently, the upper layer was formed by coating the surface of the lower layer with a mixed solution to a thickness of 110 μm, the mixed solution containing a water solution with a hydroxyethyl starch concentration of 14 wt %, with 0.25 wt % human growth hormone contained therein as a drug and FITC also contained therein so as to have an FITC concentration of 0.001 wt %. The viscosity of the lower layer produced as described above was 2 Pa·s. The viscosity of the upper layer produced as described above was 2 Pa·s. The lower layer and the upper layer had the same viscosity,

Comparative Example 2

Comparative Example 2 is a case Where the transdermal absorption sheet 1 was produced with the viscosity of the lower layer set higher than the viscosity of the upper layer.

That is, a water solution with a sodium chondroitin sulfate concentration of 40 wt % was applied onto the support 2 to a thickness of approximately 300 μm and dried at 35° C. and at a relative humidity of 40% to form the lower layer. A mixed solution was prepared by adding human growth hormone as a drug and FITC, to a water solution with a hydroxyethyl starch concentration of 14 wt % so as to have a human growth hormone concentration of 0.25 wt % and an FITC concentration of 0.001 wt %. Subsequently, the upper layer was formed by coating the surface of the lower layer with the prepared mixed solution to a thickness of 110 μm. The viscosity of the upper layer produced as described above was 200 Pa·s. The viscosity of the lower layer produced as described above was 10 Pa·s. The upper layer had a higher viscosity than the lower layer, (Evaluation Method for Test Results)

For the transdermal absorption sheets in Examples 1 to 9 and Comparative Examples 1 and 2 produced as described above, the following was examined: the filling rate at which the microneedles 10 (needle-like protruding portions) were filled with the second transdermal absorption material solution 20B containing the drug, with respect to the total amount of the second transdermal absorption material solution 20B. This enabled evaluation of how the drug was successfully concentrated at the portion of the microneedles 10. As a measuring method for the filling rate, the following two methods were adopted.

<Measuring Method for the Filing Rate 1>

In a measuring method for the filling rate 1, a confocal florescence microscope (manufactured by NIKON CORPORATION; C1plus+TE2000U (product number)) was used to observe the transdermal absorption sheet 1 to measure the rate of the FITC fluorescence intensity of the portion of the microneedies 10 with respect to the FITC fluorescence intensity of the entire transdermal absorption sheet. FITC was contained only in the second transdermal absorption material solution 20B for forming the upper layer. The filling rate at which the portion of the microneedles 10 was filled with the second transdermal absorption material solution 20B could be determined by measuring the rate of the FITC fluorescence intensity of the portion of the microneedles.

<Measuring Method for the Filling Rate 2>

In a measuring method for the filling rate 2, the portion of the microneedies of the transdermal absorption sheet 1 was cut off and dissolved in water to obtain a first solution. Moreover, the entire transdermal absorption sheet 1 except for the portion of the microneedles was also dissolved in water to obtain a second solution. The weight of the drug (human growth hormone) contained in each of the first and second solutions is quantified using Coomassie (Bradford) Protein Assay Kit (manufactured by Thermo Fisher Scientific K.K.). The filling rate was determined to be a rate of the drug amount contained in the portion of the microneedles with respect to the total drug amount. The measuring method for the filling rate 2 enabled direct evaluation of how the drug was successfully concentrated at the microneedles 10.

(Evaluation Criteria for the Filling Rate)

Rank A . . . 80% or more of the drug was concentrated at the microneedles. Very good.

Rank B . . . 60% or more and 80% or less of the drug was concentrated at the microneedles. Good.

Rank C . . . Only 50% or more and 60% or less of the drug was concentrated at the microneedles. Bad.

Rank D . . . Only less than 50% of the drug was concentrated at the microneedles. Very had.

Rank B and higher were defined to be above an acceptance line.

(Results of Test 1)

A table in FIG. 13 depicts the results of tests on Examples 1 to 9 and Comparative Examples 1 and 2. Numerical values of the filling rate in FIG. 13 were obtained using the measuring method for the filling rate 1, but the results of the evaluation method 2 are similar to the results of the evaluation method 1.

As seen in the table in FIG. 13, in Examples 1 to 9 that use the manufacturing method for the transdermal absorption sheet 1 in the present invention, the filling rate was 62% or more. In particular, in Examples 1, 2, and 5 to 9 that meet the conditions that: the upper layer has a viscosity of 2 to 10 Pa·s; the lower layer has a viscosity of at least 200 Pa·s; and the viscosity of the lower layer is at least 20 times higher than the viscosity of the upper layer, the filling rate was 80% or more. This indicates that the drug very favorably concentrated at the microneedles 10.

On the other hand, for the transdermal absorption sheet in which the lower layer and the upper layer had the same viscosity as in Comparative Example 1, the filling rate was 51%. This indicates that approximately half of the drug used was present in the areas other than the microneedles 10. Furthermore, for the transdermal absorption sheet in which the upper layer had a higher viscosity than the lower layer as in Comparative Example 2, the filling rate was 20%. This indicates that most of the drug failed to concentrate at the portion of the microneedles.

The above-described comparative results between the examples and the comparative examples indicate that the present invention allows the drug to concentrate at the microneedles 10 (needle-like protruding portions). Moreover, the viscosity of the upper layer is lower than the viscosity of lower layer so that the upper layer easily enter the needle-like recessed portion.

Test 2

In Test 2, the transdermal absorption sheet 1 was produced using an influenza vaccine (influenza HA vaccine manufactured by DENKA SEIKEN Co., Ltd.) as a drug, and the drug amount concentrated at the portion of the microneedles was checked.

That is, a mixed water solution with a hydroxyethyl starch concentration of 39 wt % and a sodium hyaluronate concentration of 1 wt % was applied onto the support 2 to a thickness of approximately 300 μm, and dried at 35° C. and at a relative humidity of 40% to form the lower layer. A mixed solution was prepared by adding the influenza vaccine as a drug to a water solution with a hydroxyethyl starch concentration of 14 wt % so as to have a influenza vaccine concentration of 0.1 wt %. Subsequently, the upper layer was formed by coating the surface of the lower layer with the prepared mixed solution to a thickness of 110 μm. Thus, the two-layer film 20 was formed on the support 2. The viscosity of the lower layer produced as described above was 1,000 Pa·s. The viscosity of the upper layer produced as described above was 2 Pa·s. The lower layer had a viscosity 500 times higher than the viscosity of the upper layer. The other conditions under which the transdermal absorption sheet 1 is manufactured were similar to the conditions in Test 1.

Then, the influenza vaccine contained in the portion of the microneedles was quantified as follows. That is, the portion of the microneedles was cut off and dissolved in water to obtain a solution. Then, a weight of the influenza vaccine contained in the resultant solution was quantified using the Coomassie (Bradford) Protein Assay Kit. As a result of the quantification, the weight of the influenza vaccine in the portion of the microneedles was 1.4 μg, which was 83% of an influenza vaccine weight of 1.7 μg contained in the whole transdermal absorption sheet.

The results of Test 2 indicate that implementation of the manufacturing method for the transdermal absorption sheet in the present invention allows a filling rate of 83% to be achieved to concentrate the drug at the portion of the microneedles even when the influenza vaccine is used as the drug.

In Test 2, the drug amount was directly measured using the above-described <Measuring Method for the Filling Rate 2>. When the <Measuring Method for the Filling Rate 1> was used for the measurement, the filling rate was 82%, that is, similar results were obtained.

Test 3

Test 3 is a case where the present invention was carried out using a type of transdermal absorption material different from the transdermal absorption material used in Test 1.

That is, a mixed water solution with a dextran (manufactured by Meito Sangyo Co., Ltd., dextran 70) concentration of 39 wt % and a sodium hyaluronate concentration of 1 wt % was applied onto the support 2 to a thickness of approximately 300 μm, and dried at 35μC. and at a relative humidity of 40% to form the lower layer. A mixed solution was prepared by adding human growth hormone as a drug and FITC to a water solution with a dextran concentration of 14 wt %, so as to have a human growth hormone concentration of 0.25 wt % and an FITC concentration of 0.001 wt %. Subsequently, the upper layer was formed by coating the surface of the lower layer with the prepared mixed solution to a thickness of 110 μm. The viscosity of the lower layer produced as described above was 1,000 Pa·s. The viscosity of the upper layer produced as described above was 1 Pa·s. The lower layer had a viscosity 1,000 times higher than the viscosity of the upper layer. As to the other conditions, the transdermal absorption sheet 1 was produced under conditions similar to the conditions in Test 1.

The filling rate of the transdermal absorption sheet 1 produced as described above was evaluated in a manner similar to the manner in Test 1. The result was 82% which was a good result.

The results of Test 3 indicate that implementation of the manufacturing method for the transdermal absorption sheet in the present invention allows a filling rate of 82% to be achieved to concentrate the drug at the portion of the microneedles even when the type of the transdermal absorption material is changed.

Test 4

In Test 4, the transdermal absorption sheet 1 was produced using insulin (manufactured by PEPTIDE INSTITUTE, INC.; human insulin) as a drug, and the drug amount concentrated at the portion of the microneedles was checked.

That is, a mixed water solution with a hydroxyethyl starch concentration of 48.8 wt % and a sodium hyaluronate concentration of 1.2 wt % was applied onto the support 2 to a thickness of approximately 240 μm to form the lower layer. A mixed solution was prepared by adding insulin as a drug and FITC to a water solution with a hydroxyethyl starch concentration of 50 wt %, so as to have an insulin concentration of 0.25 wt % and an FITC concentration of 0.001 wt %. Subsequently, the upper layer was formed by coating the surface of the lower layer that had not been dried with the prepared mixed solution to a thickness of 15 μm. Thus, the two-layer film 20 was formed on the support 2. The viscosity of the lower layer produced as described above was 1,000 Pa·s. The viscosity of the upper layer produced as described above was 2 Pa·s. The lower layer had a viscosity 500 times higher than the viscosity of the upper layer.

Then, insulin contained in the portion of the microneedles was quantified as follows. That is, the portion of the microneedles was cut off and dissolved in water to obtain a solution. Then, a weight of insulin contained in the resultant solution was quantified using a commercially available Insulin Human ELISA kit. As a result of the quantification, the weight of insulin in the portion of the microneedles was 0.48 μg, which was 82% of an insulin weight of 0.58 μg contained in the whole transdermal absorption sheet.

The results of Test 4 indicate that implementation of the manufacturing method for the transdermal absorption sheet in the present invention allows a filling rate of 82% to be achieved to concentrate the drug at the portion of the microneedles even when insulin is used as the drug.

In Test 4, the drug amount was directly measured using the above-described measuring method for the filling rate. When the <Measuring Method for the Filling Rate 1> was used for the measurement, the filling rate was 82%, that is, similar results were obtained.

Test 5

In Test 5, the transdermal absorption sheet 1 was produced using bisphosphonate (manufactured by Wako Pure Chemical Industries, Ltd.; sodium risedronate) as a drug, and the drug amount concentrated at the portion of the microneedles was checked.

That is, a mixed water solution with a hydroxyethyl starch concentration of 39 wt % and a sodium hyaluronate concentration of 1 wt % was applied onto the support 2 to a thickness of approximately 300 μm, and dried at 35° C. and at a relative humidity of 40% to form the lower layer. A mixed solution was prepared by adding bisphosphonate as a drug to a water solution with a hydroxyethyl starch concentration of 14 wt %, so as to have a bisphosphonate concentration of 0.1 wt %. Subsequently, the prepared mixed solution was applied onto the lower layer to a thickness of 110 μm, and then dried at 35° C. and at a relative humidity of 40% to form the upper layer. Subsequently, water was applied onto the upper layer for humidification so as to have a thickness of 100 μm. Thus, the two-layer film 20 was formed on the support 2. The viscosity of the lower layer produced as described above was 1,000 Pa·s. The viscosity of the upper layer produced as described above was 2 Pa·s. The lower layer had a viscosity 500 times higher than the viscosity of the upper layer.

Then, the bisphosphonate contained in the portion of the microneedles was quantified as follows. That is, the portion of the microneedies was cut off and dissolved in water to obtain a solution. Then, a weight of the bisphosphonate contained in the resultant solution was quantified using LC-MS. As a result of the quantification, the weight of the bisphosphonate in the portion of the microneedles was 0.48 μg, which was 82% of a bisphosphonate weight of 0.58 μg contained in the whole transdermal absorption sheet.

The results of Test 5 indicate that implementation of the manufacturing method for the transdermal absorption sheet in the present invention allows a filling rate of 82% to be achieved to concentrate the drug at the portion of the microneedles even when the bisphosphonate is used as the drug.

In Test 5, the drug amount was directly measured using the above-described measuring method for the filling rate. When the <Measuring Method for the Filling Rate 1> was used for the measurement, the filling rate was 82%, that is, similar results were obtained.

Test 6

In Test 6, the present invention was carried out using a transdermal absorption material with a three-layer configuration of a lower layer, an intermediate layer, and an upper layer.

That is, a mixed water solution with a hydroxyethyl starch concentration of 39 wt % and a sodium hyaluronate concentration of 1 wt % was applied onto the support 2 to a thickness of approximately 260 μm, and dried at 35° C. and at a relative humidity of 40% to form the lower layer. Subsequently, a water solution with a hydroxyethyl starch concentration of 40 wt % was applied onto the lower layer to a thickness of approximately 40 μm, and dried at 3.5° C. and at a relative humidity of 40% to form the intermediate layer. A mixed solution was prepared by adding human growth hormone as a drug and FITC to a water solution with a hydroxyethyl starch concentration of 14 wt %, so as to have a human growth hormone concentration of 0.25 wt % and an FITC concentration of 0.001 wt %. Subsequently, the upper layer was formed by coating the surface of the intermediate layer with the prepared mixed solution so as to have a thickness of 110 μm, The viscosity of the lower layer produced as described above was 1,000 Pa·s. The viscosity of the intermediate layer produced as described above was 2 Pa·s. The viscosity of the upper layer produced as described above was 2 Pa·s. The viscosity difference between the lower layer and the upper layer corresponded to 500 times. As to the other conditions, the transdermal absorption sheet was produced under the conditions similar to Test 1.

The filling rate of the transdermal absorption sheet produced as described above was evaluated in a manner similar to the manner in Test 1. The result was 82% and was a good result.

The results of Test 6 indicate that implementation of the manufacturing method for the transdermal absorption sheet in the present invention allows a filling rate of 82% to be achieved to concentrate the drug at the portion of the microneedles even when the three-layer configuration is used as the transdermal absorption sheet material.

What is claimed is:

1. A manufacturing method for a transdermal absorption sheet in which a plurality of fine needle-like protruding portions are arranged in a two-dimensional array on a surface of a sheet portion supported by a support, the method comprising:
    a laminating step of forming, on the support, a multilayer film which comprises a plurality of layers containing a transdermal absorption material, wherein the plurality of layers satisfy $V1>V2\geq \ldots \geq Vn \geq \ldots \geq Vt$ when a lowermost layer is represented as a first layer, an uppermost layer is represented as a t-th layer ($t\geq 2$) and a viscosity of an n-th layer is represented as Vn, and at least one layer other than the lowermost layer contains a drug;
    a filling step of pressing a mold in which needle-like recessed portions corresponding to inverted needle-like protruding portions are arranged in a two-dimensional array, against a surface of the multilayer film supported by the support to allow the multilayer film to flow and filling the needle-like recessed portions with a solution of the transdermal absorption material;
    a solidifying step of solidifying the multilayer film in a state where the mold is pressed against the surface of the multilayer film; and
    a peeling-off step of peeling the solidified multilayer film from the mold.

2. The manufacturing method for the transdermal absorption sheet according to claim 1, wherein a viscosity of the lowermost layer is at least twice as high as a viscosity of the uppermost layer.

3. The manufacturing method for the transdermal absorption sheet according to claim 1, wherein a viscosity of the uppermost layer is 2 to 30 Pa·s.

4. The manufacturing method for the transdermal absorption sheet according to claim 1, wherein an air vent hole is formed at a tip of each of the needle-like recessed portions in the mold.

5. The manufacturing method for the transdermal absorption sheet according to claim 1, wherein the transdermal absorption material is a water-soluble polymer substance.

6. The manufacturing method for the transdermal absorption sheet according to claim 1, wherein a transdermal absorption material in at least one of the plurality of layers containing the transdermal absorption material is composed of a plurality of water-soluble polymer substances.

7. The manufacturing method for the transdermal absorption sheet according to claim 5, wherein at least one of the water-soluble polymer substances is any one of hydroxyethyl starch, dextran, chondroitin sulfate, hyaluronic acid, and carboxymethyl cellulose.

8. The manufacturing method for the transdermal absorption sheet according to claim 1, wherein the drug is any one od peptide, protein, nucleic acid, polysaccharide, a vaccine, a medical compound belonging to a water-soluble low-molecular-weight compound, and a cosmetic component.

9. A manufacturing method for a transdermal absorption sheet in which a plurality of fine needle-like protruding portions are arranged in a two-dimensional array on a surface of a sheet portion supported by a support, the method comprising:
    a laminating step of forming a multilayer film on the support by applying solutions containing transdermal absorption material, the multilayer film comprising a plurality of layers which satisfy $V1>V2\geq \ldots \geq Vn \geq \ldots \geq Vt$ when a lowermost layer is represented as a first layer, an uppermost layer is represented as a t-th layer ($t\geq 2$) and a viscosity of an n-th layer is represented as Vn, and at least one layer other than the lowermost layer contains a drug;
    a filling step of pressing a mold in which needle-like recessed portions corresponding to inverted needle-like protruding portions are arranged in a two-dimensional array, against a surface of the multilayer film supported by the support to allow the multilayer film to flow and filling the needle-like recessed portions with a solution of the transdermal absorption material;

a solidifying step of solidifying the multilayer film in a state where the mold is pressed against the surface of the multilayer film; and a peeling-off step of peeling the solidified multilayer film from the mold, wherein the multilayer film flows when the mold is pressed against the surface of the multilayer film to apply a pressure to the surface in the filling step.

* * * * *